United States Patent
Stekker et al.

(10) Patent No.: US 9,566,367 B2
(45) Date of Patent: Feb. 14, 2017

(54) MAGNESIUM ALLOY AND RESORBABLE STENTS CONTAINING THE SAME

(75) Inventors: Michael Stekker, Aurich (DE); Norbert Hort, Luneburg (DE); Frank Feyerabend, Hamburg (DE)

(73) Assignees: Helmholtz-Zentrum Geesthacht Zentrum fur Material-und Kustenforschung GmbH, Geeshacht (DE); MEKO LASERSTRAHL-MATERIALBEARBEITUNGEN E.K, Sarstedt (DE)

( * ) Notice: Subject to any disclaimer, the term of this patent is extended or adjusted under 35 U.S.C. 154(b) by 55 days.

(21) Appl. No.: 14/238,875

(22) PCT Filed: Aug. 15, 2012

(86) PCT No.: PCT/EP2012/065974
§ 371 (c)(1),
(2), (4) Date: Mar. 28, 2014

(87) PCT Pub. No.: WO2013/024124
PCT Pub. Date: Feb. 21, 2013

(65) Prior Publication Data
US 2014/0222133 A1    Aug. 7, 2014

Related U.S. Application Data

(60) Provisional application No. 61/573,114, filed on Sep. 6, 2011.

(30) Foreign Application Priority Data

Aug. 15, 2011    (DE) .......................... 10 2011 110 114

(51) Int. Cl.
*C22C 23/00*    (2006.01)
*A61L 27/58*    (2006.01)
(Continued)

(52) U.S. Cl.
CPC .................. *A61L 27/58* (2013.01); *A61F 2/82* (2013.01); *A61K 31/337* (2013.01);
(Continued)

(58) Field of Classification Search
CPC ................................... A61L 27/58; A61F 2/82
See application file for complete search history.

(56) References Cited

U.S. PATENT DOCUMENTS

2006/0052863 A1    3/2006 Harder et al.
2006/0228249 A1    10/2006 Lyon et al.
(Continued)

FOREIGN PATENT DOCUMENTS

WO    2005035811    4/2005
WO    2008009825    1/2008
(Continued)

OTHER PUBLICATIONS

International Search Report for PCT/EP2012/065974 mailed on Sep. 28, 2012.
(Continued)

*Primary Examiner* — Sikyin Ip
(74) *Attorney, Agent, or Firm* — Amin, Turocy & Watson LLP

(57) ABSTRACT

The present invention is directed to a magnesium alloy containing 5.0% by wt.-25.5% by wt. dysprosium, 0.01% by wt.-5.0% by wt. neodymium and/or europium, 0.1% by wt. 3.0% by wt. zinc, 0.1% by wt.-2.0% by wt. Zirconium, and balance to 100.0% by wt. magnesium, being degradable under physiological conditions and which is particularly suitable for the production of absorbable stents and to stents made thereof.

6 Claims, 8 Drawing Sheets

(51) Int. Cl.
    *A61L 31/02*     (2006.01)
    *A61L 31/14*     (2006.01)
    *C22C 23/06*     (2006.01)
    *C22F 1/00*     (2006.01)
    *C22C 1/02*     (2006.01)
    *C22F 1/06*     (2006.01)
    *A61F 2/82*     (2013.01)
    *A61K 31/337*     (2006.01)
    *A61K 31/439*     (2006.01)
    *C25F 3/18*     (2006.01)

(52) U.S. Cl.
    CPC .......... *A61K 31/439* (2013.01); *A61L 31/022* (2013.01); *A61L 31/148* (2013.01); *C22C 1/02* (2013.01); *C22C 23/06* (2013.01); *C22F 1/006* (2013.01); *C22F 1/06* (2013.01); *C25F 3/18* (2013.01)

(56) References Cited

U.S. PATENT DOCUMENTS

2007/0191708 A1   8/2007  Gerold et al.
2010/0012234 A1   1/2010  Cantrel et al.
2010/0222873 A1*  9/2010  Atanasoska et al. ........ 623/1.42
2010/0262222 A1  10/2010  Weber

FOREIGN PATENT DOCUMENTS

WO   2010118193   10/2010
WO   2011117298    9/2011

OTHER PUBLICATIONS

Database WPI, Week 199631, Thomson Scientific, London, GB, AN 1996-307016, XP002683805.

* cited by examiner

MAGNESIUM ALLOY AND RESORBABLE STENTS CONTAINING THE SAME

The present invention is directed to a magnesium alloy comprising dysprosium, being degradable under physiological conditions which is particularly suitable for the production of absorbable stents and to stents made thereof.

Nowadays, the implantation of vessel grafts, such as stents, is a common surgical intervention for the treatment of stenoses. They are usually made of metal alloys such as stainless steel or nitinol. Such metal stents are known in large numbers and have proven in practice. Due to their metallic structure and load capacity such metal stents should ensure that the vessels remain open after implantation and that the blood flow through the vessels will be ensured permanently.

However, recent investigations have shown that vascular stenoses don't have to be dilated permanently by means of an endoprosthesis, particularly in form of a stent. It is entirely sufficient to support the blood vessel temporarily because the traumatized tissue of the vessel heals and the smooth muscle cells of the vessel regenerate and resume the task of keeping the blood vessel open, and thus the stent does not need to remain longer than necessary in the vessel lumen.

Stents are currently divided into two basic types, permanent as well as degradable or absorbable stents. Permanent stents are designed such that they can remain in the vessel for an indefinite period of time. Absorbable stents, however, are degraded in the vessel over a predetermined period of time.

Currently one tries to solve the problem of restenosis after stent implantation by attempting to locally inhibit the growth of the smooth muscle cells. This is for example done with stents, which release pharmaceutically active agents that function preferably antiproliferative. These active agents are usually released from a drug-containing coating, which may be applied both to permanent and to absorbable stents.

The supporting effect by the metal structure is frequently only required for short periods of times as the body tissue can recover after the implantation of the stent and the supporting function is not needed anymore. Preferably, degradable and absorbable stents are only degraded when the traumatized tissue of the vessel has healed and the vessel re-stabilized, so that the stent does no longer have to remain in the vessel lumen. Especially in the case of stents coming in contact with blood, these cause as being a material foreign to the body, the formation of restenoses. Efforts in the development of stents, to an improved biocompatibility of the stent material, greater flexibility with decreasing material fatigue and reduction of the foreign surface should minimize the risk of stent-induced restenosis rate further and further. Here, absorbable stents have the advantage that the material foreign to the body does not permanently remain in the vessel and the risk of restenosis is therefore temporally limited. A use of absorbable stents is advantageous for children, too, since vascular growth is not adversely affected, or the stent does not need to be removed again after a while during which the child has grown.

For said reason, stents consisting of bioabsorbable materials, such as for example of polymers such as polyhydroxybutyrate or of metals such as magnesium or iron are increasingly developed in recent times and used in clinical trials.

The large restoring forces of vessels after a dilation are a major cause of restenoses. Therefore, absorbable vessel grafts must be made of a material which can be degraded well by the body, but also has a sufficiently high retention force to prevent re-stenosis of the vessel.

A stent once inserted must maintain its size and shape, despite the different forces acting on it, such as the pulsating load by the beating heart. In addition, the stent must have sufficient flexibility to be crimped onto a balloon, and later to be expanded in the vessel.

Absorbable polymers which are used for the production of stents, have lower mechanical strength than those non-absorbable metal alloys used hitherto. A compensation of this disadvantage can be achieved by greater strut widths of the stent. However, this will increase the mechanical irritation of the vessel wall during stent implantation and thus also the risk of restenosis. Absorbable stents of iron or an iron-based alloy have the disadvantage that the residence time in the vessel up to the complete degradation is longer than necessary and desired. For absorbable stents the desired period of absorption is between 3 and 12 months, wherein the mechanical load capacity must be ensured before. Magnesium is a trace element present in the body and therefore suitable as a basis for an absorbable stent. Further, alloying elements were selected from the group of the rare earth metals, as these do not naturally occur in the body. This allows a detection of the degradation products in the tissue and in the organs.

Magnesium and magnesium alloys have excellent mechanical and physical properties for a wide range of applications. Their low weight along with high strength qualifies magnesium and magnesium alloys as appropriate materials also for endoprostheses. Magnesium and magnesium alloys are very reactive and therefore susceptible to corrosion. Nevertheless these properties are desirable for absorbable implants. However, the following problems exist in the prior art: Although in principle the objective of an absorption of the implanted stent is achieved, the problem of a temporally non-defined degradation of the stent exists. Depending on the choice of material, the degradation of the material is subjected to strong fluctuations, cannot be controlled, and is generally too fast to ensure a safe ingrowth of the stent into the vessel walls. When absorption occurs too fast the absorbable stent cannot grow into the vessel wall and take over the supporting function until the regeneration of the vessel segment. It can rather detach or pieces of the stent may be detached and be swept away in the blood flow and cause life-threatening problems for the patient.

A bioabsorbable metal stent made of magnesium and yttrium is disclosed in the European patent EP 1 419 793 B1. A magnesium alloy with yttrium, neodymium and further optional components suitable for the production of stents is described in the European patent EP 2 169 090 B1. These stents have the disadvantage that they dissolve too fast and additionally uncontrolled. Since the dissolution process usually starts before the stent is grown into the vessel wall, fragments may be detached, transported through the bloodstream and cause a heart attack. Further, it has been found that these stents of a magnesium-yttrium alloy promote the deposition of calcium phosphate on the luminal surface of the stents and thereby lead to a re-occlusion of the stent (in-stent restenosis) and thus also of the vessel, which is especially to be prevented.

The European patent applications EP 2 213 314 A1 and EP 1 842 507 A1 also disclose stents of a magnesium alloy containing gadolinium. To obtain the desired mechanical properties such as strength, tension force and ductility, gadolinium is required in quantities greater than 5% by weight. At quantities greater than 5% by weight gadolinium, however, the problem arises that the processability of the alloy into a tube suitable for laser processing, and the homogeneity of the alloy is no longer guaranteed. Thus, it can be stated that until August 2012 within prior art no metal alloy exists which would be suitable as a material for the production of bioabsorbable stents.

For said reason, it is required to develop a suitable construction material for absorbable stents. The objective of the present invention consists in providing a suitable material and a vessel graft made thereof which provides its supporting function at least until the regenerated tissue itself is once again capable of taking over that function.

Summarizing the concrete objective, the objective of the present invention is to provide a magnesium alloy whose dissolution kinetics is delayed or significantly decelerated compared with the known magnesium alloys.

Said objective is solved by the technical teaching of the independent claims of the present invention. Further advantageous embodiments of the invention result from the dependent claims, the description and the examples.

It has surprisingly been found that magnesium alloys with a relatively high content of dysprosium, which is preferably further blended with neodymium and/or europium and optionally zirconium and/or zinc, are characterized by an advantageous corrosion behavior, by desired absorption kinetics and by mechanical properties suitable for the production of stents.

The present invention relates therefore to magnesium alloys, which contain the following components based on the total weight of the alloy (given in % per wt.):

| | |
|---|---|
| 64.5% by wt.-94.79% by wt. | magnesium |
| 5.0% by wt.-25.5% by wt. | dysprosium |
| 0.01% by wt.-5.0% by wt. | neodymium and/or europium. |
| 0.1% by wt.-3.0% by wt. | zinc |
| 0.1% by wt.-2.0% by wt. | zirconium. |

This alloy consists of 5.0 to 25.5% by wt. Dy and 0.01 to 5.0% per wt. Nd or 0.01 to 5.0% per wt. Eu or 0.01 to 5.0% per wt. Nd and Eu together, 0.1% by wt.-3.0% by wt. zinc and 0.1% by wt.-2.0% by wt. zirconium, wherein the remainder up to 100% per wt. is Mg. This alloy may further contain unavoidable impurities. Preferred ranges for the components Dy, Nd, Eu, Zn and Zr are described in detail further below.

The present invention relates further to magnesium alloys containing 5.0 to 25.5% by wt. Dy and 0.01 to 5.0% per wt. Nd or 0.01 to 5.0% per wt. Eu or 0.01 to 5.0% per wt. Nd and Eu together, 0.1% by wt.-2.0% by wt. zirconium further comprising 0.1% by wt.-2.0% by wt. zinc.

The present invention relates further to magnesium alloys containing 5.0 to 25.5% by wt. Dy and 0.01 to 5.0% per wt. Nd or 0.01 to 5.0% per wt. Eu or 0.01 to 5.0% per wt. Nd and Eu together, 0.1% by wt.-3.0, preferably up to 2.0% by wt. zinc, further comprising 0.1% by wt.-0.3% by wt. zirconium. These alloys, too, may further contain unavoidable impurities.

The present invention relates further to magnesium alloys, which contain the following components based on the total weight of the alloy (given in % per wt.):

| | |
|---|---|
| 81.5% by wt.-91.9% by wt. | magnesium |
| 7.0% by wt.-15.0% by wt. | dysprosium |
| 0.5% by wt.-1.5% by wt. | neodymium and/or europium |
| 0.5% by wt.-1.5% by wt. | zinc |
| 0.1% by wt.-0.5% by wt. | zirconium |

Magnesium (Mg) as main component of the alloy has been chosen because Mg is biologically degradable and a necessary element of the body which does not accumulate in the body in a way that it is harmful. Excessive magnesium is generally excreted naturally.

Dysprosium together with magnesium forms intermetallic precipitates. The high solubility of dysprosium in magnesium ensures further that one can successfully carry out the heat treatments necessary for the production of stents, that precipitates dissolve and specifically re-precipitate and one can, thus, adjust properties such as strength, ductility and corrosion behavior within large limits. A high strength and a high ductility slow down the biologically degradation of the alloy which is especially desired for a stent made of a magnesium alloy. The ductility should be at least 15%, preferably at least 20%, further preferably between 20% and 25% and especially preferred at least 25%. As herein used, the terms "ductility" and "elongation at break" are used synonymously. The yield strength as a measure for strength should be in a range from 80 MPa-180 MPa.

Dysprosium increases further the strength of the alloy, because it is dissolved in the mixed crystal and may form precipitates. Europium forms only precipitates similar to neodymium. In the individual grain of the alloys according to the invention which contain dysprosium as well as europium and/or neodymium solid solution hardening and precipitation hardening can be combined. By heat treatment one can dissolve and specifically re-precipitate the magnesium-dysprosium precipitates. In this way strength and ductility can be adjusted within a broad range by the composition of the alloy according to the invention. However, as soon as all precipitates on the grain boundaries have disappeared grains can start to grow (Ostwald-Ripening). Yet, coarse grains have a negative effect on strength and ductility and, thus, should be avoided. Magnesium-europium or magnesium-neodymium precipitates on the grain boundaries stabilize the grain boundaries during a heat treatment, which is always necessary during the production of stents. Therefore, the grain size does not change because of the stabilizing effect of europium and/or neodymium. In any case, it is desirable to stabilize an existing fine grain because, according to Hall-Petch, a fine-grained microstructure positively affects strength and ductility. According to the invention this stabilization within a Mg—Dy-alloy is achieved by the addition of europium and/or neodymium.

For the production of stents, especially strength characteristics and the corrosion behavior have been taken into consideration to provide an alloy being as strong and corrosion-resistant as possible.

It has been found that a magnesium alloy according to the invention having a content of 10% by weight Dy shows the minimum of corrosion. Thus, it is especially preferred if the content of dysprosium in the inventive alloys is approximately 10% by weight±2% by weight. FIG. 7 shows in regard to the corrosion that a binary magnesium alloy containing dysprosium with an amount between 7 to 15% by weight, even better 8-12% by weight dysprosium has a preferred minimal corrosion behavior. The corrosion is the crucial property for the degradation rate of the stent in the vessel. It is important that a biodegradable stent does not lose its stability too soon so that no fragments detach and the stability is guaranteed by the stent until it can be again secured by the vessel alone and until the stent has grown into the vessel wall.

Neodymium and europium, too, did not show negative effects on cells in vitro. Europium in comparison to neodymium has even been tolerated a little better. Both elements are virtually insoluble in magnesium and form intermetallic phases with magnesium which are not dissolved also not by the heat treatments essential for the production of stents. These precipitates are localized on the grain boundaries and stabilize them so that the fine grain of metal forming is maintained. According to the invention it has been shown that 1% by weight of neodymium or 1% by weight of europium or 1% by weight of europium and neodymium together is sufficient. With quantities of europium and/or neodymium of more than 1% by weight the ductility of the alloy starts to decrease, which is undesirable for the production of stents and quantities of europium and/or neodymium of more than 2% by weight reduce the ductility of the alloy in such a way that the essential minimal ductility of 15% was not guaranteed any more. Quantities of Eu and/or Nd of more than 2% by weight lead to an increase in the embrittlement of the alloy and a decrease of the ductility with further increasing weight proportion.

But in particular the ductility of an alloy is essential for the suitability as a construction material for stent production. After the manufacturing the stent is crimped on a carrier, mostly a catheter balloon, and thereby plastically deformed for the first time. Subsequently, in situ in the blood vessel, the stent is expanded and plastically deformed once more. A high elongation at break and thus a high ductility is necessary to be able to carry out these rather drastically deformations without damage. Simultaneously, a high strength is also necessary to avoid break of the stent struts during these two deformations and to prevent a compression of the stent and thus the occlusion of the vessel by the restoring forces of the vessel wall. Among the possible strengthening mechanisms the Hall-Petch-Mechanism (grain-boundary strengthening) is suitable to achieve high strength and simultaneously increase the ductility. All alloying elements, the intermetallic phases resulting therefrom and also the cold deformation created by the deformation of the stent increase the strength but decrease the ductility at the same time. To counteract this, a fine grain is indispensable.

Zinc improves the casting characteristics of the magnesium alloy and has a strengthening effect. Thus, the fatigue behavior and tensile strength can be increased by addition of zinc up to 3% by weight. The tensile strength should preferably be as high as possible and preferably more than 180 MPa (≥180 MPa), further preferred more than 200 MPa (≥200 MPa). However, the tendency for hot crack formation increases with more than 1% by weight Zn (see FIG. 8). Thereby, micropores are formed, which negatively affect tensile strength and ductility of an alloy. They act as inner notches so that in tensile tests a construction material fails generally clearly below the maximal achievable strength at a fractional amount of the theoretical ductility. In general, a disadvantageous effect on the processing behavior and to the mechanical properties of the alloys according to the invention shows with more than 2% by weight zinc. Zinc is an essential element for human beings, which is part of many enzymes and has many functions. Among others, zinc has an anti-inflammatory effect. Nevertheless, with high doses acute poisoning can occur and a long-term supply causes disorders, especially of the iron and copper metabolism (cf. Guidelines for drinking-water quality, World Health Organization, 1996). Therefore, toxic side effects cannot be excluded with a content of 4% by weight zinc and more. The amount of zinc should, thus, be below 2.0% by weight, preferred below 1.8% by weight, more preferred below 1.6% by weight, even more preferred below 1.4% by weight and especially preferred below 1.2% by weight. One should not fall below 0.1% by weight Zn, preferably 0.3% by weight Zn and especially 0.5% by weight Zn as lower limit.

Zirconium (Zr) may be present in the magnesium alloy in addition to zinc or also instead of zinc. According to the invention Zr is used as grain refiner. Further Zr can bind Fe and, thus, reduce its content further. It has been found that elementary iron increases the corrosion which should be avoided according to the invention. This could be explained by the fact that iron together with magnesium forms a galvanic element, whereas also other reasons are conceivable. According to the invention one alloys Zr in a range up to approximately 0.4% by weight. Also larger amounts of Zr of 2% by weight or even 3% by weight result in a similar well grain refinement, but increase the price of the alloy remarkably and, in addition, lead to an embrittlement of the alloy, which in turn leads to a decrease of the ductility. Zr and Mg show a peritectic reaction in the Mg-rich corner of their phase diagram. This means that during solidification primary pure Zr precipitates. Due to the hexagonal lattice structure and lattice parameters which are very similar to that of Mg, Zr functions as grain refiner. Thereby, the Zr—nucleation sites have to reach first a diameter of about 2 μm or more. However, Zr has a substantially higher density than Mg. Therefore, the Zr-particles in a Mg-melt drop comparably fast to the ground. Thus, only the half of the Zr content of 1% by weight used is effectively exploitable as grain refiner. In general, the remaining part precipitates at the bottom of the crucible. Stirring during solidification can be used successfully to suppress this sedimentation. However, this is expensive and not suitable under any conditions. As a rule one loses therefore approximately half of the Zr used. This is among others an essential matter of expense. Since, in regard to grain refinement, the results achieved with clearly smaller quantities of Zr of 0.05% by weight to 0.50% by weight were as good as with 1% by weight, 2% by weight or 3% by weight and in addition with an amount of Zr below 0.50% by weight no embrittlement occurs, 0.05% by weight to 0.50% by weight and further preferred 0.08% by weight to 0.40% by weight Zirconium are used according to the invention.

The influence of Zr has been exemplarily examined with the magnesium alloy containing 10% by weight Dy and 1% by weight Nd. Permanent mold direct chill casting ("Tütengußverfahren") has been used as production process. For construction materials produced by permanent mold direct chill casting, one can assume that a cast part shows a homogenous microstructure and that the alloying elements are homogenously distributed, too. However, the structure is comparatively rough and the grain size is in the range of several millimeters (FIG. 1). The inventors could show that addition of only 0.6% by weight Zr led to a clear reduction of grain size (FIG. 2). Therefore, three differently large proportions of Zr (0.2, 0.4, 0.6% by weight) and their influence to the structure forming have been examined. For determining the grain size the linear intercept method (also known as average grain intercept method) has been applied. Surprisingly already a small proportion of 0.2% by weight results in a clear grain refinement (FIG. 2) and the grain size is in the range of about 102 μm. Addition of 0.4 or 0.6% by weight results in grain sizes of about 68 μm, respectively 64 μm (FIGS. 4 and 5). One can therefore conclude that already an addition of 0.2% by weight Zr causes an effective grain refinement and that surprisingly the total amount of Zr can be activated for grain refinement. This reduces the costs for Zr alone by about 50%.

Therefore, it is preferred, if according to the invention an alloy has further 0.02-0.80% by weight, preferred 0.04-

0.60% by weight, preferred 0.05-0.55% by weight, further preferred 0.06-0.50% by weight, even more preferred 0.07-0.45% by weight, even more preferred 0.08-0.40% by weight, even more preferred 0.09-0.35% by weight, even more preferred 0.10-0.30% by weight, even more preferred 0.12-0.28% by weight and especially preferred 0.15-0.25% by weight Zirconium.

The grain sizes have been determined according to the known linear grain intercept method. During linear grain intercept method counting the grain size in the ocular is done on a focusing screen or on photographic images. The lines can be either straight or circular. Grains which are only cut half at the end of the line counted herewith as half grains. The magnification is chosen such that at least 50 grains are cut by the grid. At least 5 sites with a total number of at least 250 intercept points on the sample are examined.

The present invention relates further to magnesium alloys, which contain the following components based on the total weight of the alloy (given in % per wt.):

| | |
|---|---|
| 80.7% by wt.-94.7% by wt. | magnesium |
| 5.0% by wt.-15.0% by wt. | dysprosium |
| 0.1% by wt.-2.0% by wt. | neodymium |
| 0.1% by wt.-2.0% by wt. | zinc |
| 0.1% by wt.-0.3% by wt. | zirconium |

Optionally, the amount of neodymium in this alloy may be substituted by europium, or one may add further 0.1% by wt.-2.0% by wt europium.

It goes without saying that all components of an alloy must add up to 100% by wt. If above alloy contains 15.0% by wt. dysprosium (Dy) and 2.0% by wt. neodymium (Nd) then the magnesium content cannot exceed 83% by wt. If other components are present besides magnesium, dysprosium, neodymium/europium, zinc and zirconium, then those are the impurities described herein such as for example, the other metals, metal salts, non-metals, carbon, sulfur, nitrogen, oxygen, silicon and/or hydrogen.

Unless specifically listed, the herein disclosed alloys may contain unavoidable impurities, which are in the range of the lower detection limit or in the range of 1 ppm up to 0.4% by wt., preferably up to 0.3% by wt., further preferably up to 0.2% by wt., and in particular preferably up to 0.1% by wt. Silicon as main ingredient of the impurities may reach already 0.3% by weight. It is therefore especially preferred if the unavoidable impurities except silicon represent in total less than 0.3% by weight, preferred less than 0.2% by weight, further preferred less than 0.1% by weight, further preferred less than 0.05% by weight, further preferred less than 0.01% by weight, further preferred less than 0.001% by weight, further preferred less than 500 ppm and especially preferred less than 300 ppm. The aforementioned percentages refer to the sum of all impurities except silicon and not to the individual impurity. These impurities (including silicon) may also be present in the alloy in an amount of 1 ppm up to 0.4% by wt. or 0.3% by wt. or 0.2% by wt., if they are not explicitly listed as an alloying element and, in the case not being mentioned, are added to the weight proportion of that component of the alloy, along which they have come into the alloy. Nevertheless preferred is when the impurities except silicon do not exceed each an amount of 500 ppm, preferred 300 ppm, further preferred below 200 ppm and especially preferred 150 ppm. Silicon can be a major component of the impurities and exist in the alloy up to 0.3% by wt., preferably up to 0.2% by wt. and more preferably up to 0.1% by wt. Depending on how the magnesium is extracted the magnesium may contain a varying high content of silicon. If very pure magnesium is used the content of Si in the alloy can also be below 400 ppm, preferred below 300 ppm, further preferred below 250 ppm and especially preferred below 200 ppm.

The invention further comprises magnesium alloys composed of the following components based on the total weight of the alloy:

| | |
|---|---|
| 76.0% by wt.-95.0% by wt. | magnesium |
| 5.0% by wt.-25.5% by wt. | dysprosium |
| 0.0% by wt.-5.0% by wt. | neodymium |
| 0.0% by wt.-5.0% by wt. | europium |
| 0.0% by wt.-3.0% by wt. | zinc |
| 0.0% by wt.-1.5% by wt. | zirconium |
| 0.0% by wt.-1.0% by wt. | other metals, metal salts and non metals, which are commonly referred to as impurities. |

It is preferred, when the alloy of the invention comprises 5.0-25.5% by wt., preferably 5.2-22.0% by wt., more preferred 5.4-20.0% by wt., more preferred 5.5-19.0% by wt., more preferred 5.6-18.0% by wt., more preferred 5.7-17.0% by wt., more preferred 7.0-17.0% by wt., more preferred 7.5-16.5% by wt., more preferred 5.8-16.0% by wt., more preferred 8.0-16.0% by wt., more preferred 5.9-15.0% by wt., more preferred 8.3-15.8% by wt., more preferred 8.5-15.5% by wt., more preferred 8.7-15.0% by wt., more preferred 6.0-14.0% by wt., more preferred 8.8-14.8% by wt., more preferred 8.9-14.5% by wt., more preferred 9.0-14.0% by wt., more preferred 6.1-13.0% by wt., more preferred 9.1-13.5% by wt., more preferred 9.2-13.0% by wt, more preferred 6.2-12.5% by wt., more preferred 9.3-12.7% by wt., more preferred 9.4-12.4% by wt., more preferred 6.3-12.0% by wt., more preferred 9.5-12.2% by wt., more preferred 9.5-12.0% by wt., more preferred 6.4-11.5% by wt, more preferred 9.5-11.5% by wt., more preferred 6.5-11.0% by wt., and more preferred 9.5-11.0% by wt. dysprosium.

Preferably, the amount of neodymium is in the range of 0.0 to 8.0% by wt., more preferably from 0.1 to 5.0% by wt., still more preferably 0.2 to 4.0% by wt., even more preferably 0.3 to 3.0% by wt., still more preferably 0.4 to 2.0% by wt. and especially preferably of 0.5 to 1.5% by wt.

Together with neodymium (Nd) or instead of Nd also europium (Eu) can be included in the alloy in proportions from 0.0 to 8.0% by wt., more preferably 0.1 to 5.0% by wt., even more preferably 0.2 to 4.0% by wt., still more preferably 0.3 to 3.0% by wt., still more preferably 0.4 to 2.0% by wt. and especially preferably from 0.5-1.5% by wt.

It is also preferred that the shared proportion of Nd and Eu in the alloy is from 0.01 to 8.0% by wt., more preferably from 0.1 to 5.0% by wt., still more preferably 0.2-4.0% by wt., still more preferably 0.3 to 3.0% by wt., still more preferably 0.4 to 2.0% by wt. and especially preferably from 0.5 to 1.5% by wt.

The sum of the weight proportions of dysprosium and neodymium is preferably in the range of 5.1 to 23.0% by wt., more preferably between 6.6 to 15.5% by wt., even more preferably, and particularly preferably from 8.4 to 13.0% by wt.

It is also preferred that the alloy according to the invention comprises furthermore 0.2 to 4.0% by wt., even more preferably 0.3 to 3.0% by wt., still more preferably 0.4 to 2.0% by wt., even more preferably 0.5 to 1.5% by wt. and especially preferably 0.7 to 1.3% by wt. zinc (Zn).

In addition to the components mentioned before a magnesium alloy of the invention may also comprise 0.0% by wt.-1.0% by wt., preferably 0.1% by wt.-0.6% by wt., more preferably 0.2% by wt.-0.4% by wt. and especially preferred in total not more than 0.3% by wt. other metals, metal salts, non-metals, carbon, sulfur, silicon, nitrogen, oxygen, and/or hydrogen. These other components are impurities which are in the aforementioned small amounts harmless for the product properties or the properties of the alloy. These are essentially Fe and Si, which can enter during the production of the primary magnesium by the necessary application of FeSi during the Pidgeon-Process or by the general use of steel-tools during the processing and handling of magnesium and the magnesium alloys. Preferred is, however, that the metals Cu, Ni, Fe are each present below 300 ppm, preferably below 200 ppm and more preferably below 150 ppm. The heavy metals, especially Fe, Cu and Ni as more noble components form with magnesium a galvanic element and thus, increase the corrosion, especially in contact with a corrosive agent such as blood, in which chloride ions are present. Hydrogen is formed in the aqueous medium, so that stress corrosion cracking occurs, which should be avoided with implants and especially vascular implants such as stents. Therefore Cu, Ni, Fe extremely deteriorate the corrosion behavior, if more than the mentioned quantities are present. Commonly Cu and Ni enter magnesium alloys via recycling processes and can be avoided if one uses pure primary magnesium.

Silicon (Si) should not in be present in amounts greater than 0.4% by wt., preferably greater than 0.3% by wt. and more preferably greater than 0.2% by wt., because Si affects the properties of the alloy and the product properties negatively, so addition of silicon deteriorates the castability. Stable silicides (Mg$_2$Si) may be formed. The material embrittles with increasing amount of Mg$_2$Si precipitates. Mg$_2$Si forms additionally needles and, thus, results in a large notch effect and a low elongation at break. However, a high elongation at break is necessary for stents and a risk for cancer should obligatorily be prevented.

Furthermore it is preferred that the elements beryllium, aluminium and manganese are each present below 300 ppm, preferably below 200 ppm and more preferably below 150 ppm. Beryllium, beryllium oxide and beryllium salts are toxic for humans and are classified as carcinogenic. Beryllium may cause skin, lung, spleen and liver damages. Beryllium accumulates preferably in bones, the kidney and in the cells of the reticuloendothelial system of liver, spleen and lymph nodes and induces formation of tumors after latency lasting for years. Therefore, if possible, beryllium should totally be avoided in a degradable vascular implant. Therefore it is preferred that the alloy does not contain beryllium. Manganese as trace element is essential for humans and an important part of enzymes. But furthermore, manganese is also neurotoxic and damages the central nervous system. By a chronic, excessive long-term exposure a dementia illness with symptoms similar to Parkinson's disease, like motor impairments, may occur. A role for aluminium in Alzheimer's disease is assumed, too, aluminium is believed to accelerate, if not even causing, the onset of Alzheimer's disease. At least aluminium has been detected in plaques in the brain of Alzheimer's patients. Therefore, manganese and aluminium should be totally avoided as components of a degradable vascular implant which degrades over long-term, also from the aspect of the marketing.

La, Ce, Pr and Sm belong to the other metals or non-metals, which individually or together may be contained in the alloy in a maximum amount of 0.3% by wt., preferably 0.2% by wt. and more preferably 0.1% by wt. Whereas the following elements should be avoided or be contained in the alloy together in a maximum amount of 0.1° A, by wt., preferably 0.05% by wt., more preferably 0.01% by wt, even more preferably 0.005% by wt and even more preferably 0.001% by wt: Tb, Ho, Er, Tm, Yb and Lu. Thus, it is preferred that the magnesium alloys according to the invention and the stents produced thereof contain in total not more than 0.1% by wt., preferably 0.05% by wt. and more preferably 0.01% by wt of the elements terbium, holmium, erbium, thulium, ytterbium and lutetium, wherein further preferred these elements should be totally avoided, which means being present as impurities in the ppm-range each below 150 ppm and especially preferred below 100 ppm.

The maximum amount of 1.0% by wt. impurities comprises the other metals or non-metals such as silicon, carbon, oxygen, nitrogen, hydrogen or sulfur, also when those are additionally listed explicitly.

Surprisingly, it has been found that, notwithstanding the relatively high amount of dysprosium, the alloys according to the invention and respectively the stents made thereof are not radio-opaque. The angiography carried out within the animal experiments showed that the stents were not opaque, which means that they were not visible on the X-ray images during the coronary angiography (see FIGS. 6A-AD). This allows that one can clearly see the vessel lumen via application of a contrast agent. Thereby one can non-invasively track the healing process and the control with respect to possible in-stent-restenoses in the patients, which means by imaging procedures like MRT or CT. It is therefore preferred that the alloys according to the invention are not visible by X-ray or not radio-opaque. If the stents should still be visible in the X-ray image so that correct positioning can be checked one may attach radio-opaque markers to specific sites of the stent or the catheter balloon used for implantation of that stent, which is regularly done in practice.

One preferred composition of a magnesium alloy of the invention comprises or consists of:

| | |
|---|---|
| 77.0% by wt.-94.6% by wt. | magnesium |
| 5.0% by wt.-15.0% by wt. | dysprosium |
| 0.2% by wt.-4.0% by wt. | neodymium |
| 0.2% by wt.-4.0% by wt. | zinc |

One preferred composition of a magnesium alloy of the invention comprises or consists of:

| | |
|---|---|
| 88% by wt. | magnesium |
| 10% by wt. | dysprosium |
| 1% by wt. | neodymium |
| 1% by wt. | zinc |

One preferred composition of a magnesium alloy of the invention comprises or consists of:

| | |
|---|---|
| 79.0% by wt.-94.75% by wt. | magnesium |
| 5.0% by wt.-15.0% by wt. | dysprosium |
| 0.2% by wt.-4.0% by wt. | neodymium |
| 0.05% by wt.-2.0% by wt. | zirconium |

One further, preferred composition of a magnesium alloy of the invention comprises or consists of:

| 88% by wt. | magnesium |
|---|---|
| 10% by wt. | dysprosium |
| 1% by wt. | neodymium |
| 1% by wt. | zirconium |

One preferred composition of a magnesium alloy of the invention comprises or consists of:

| 75.0 by wt.-94.55% by wt. | magnesium |
|---|---|
| 5.0% by wt.-15.0% by wt. | dysprosium |
| 0.2% by wt.-4.0% by wt. | neodymium |
| 0.2% by wt.-4.0% by wt. | zinc |
| 0.05% by wt.-2.0% by wt. | zirconium |

One especially preferred composition of a magnesium alloy of the invention comprises or consists of:

| 87% by wt. | magnesium |
|---|---|
| 10% by wt. | dysprosium |
| 1% by wt. | neodymium |
| 1% by wt. | zinc |
| 1% by wt. | zirconium |

One preferred composition of a magnesium alloy of the invention comprises or consists of:

| 76.0% by wt.-94.5% by wt. | magnesium |
|---|---|
| 5.0% by wt.-15.0% by wt. | dysprosium |
| 0.2% by wt.-4.0% by wt. | neodymium |
| 0.2% by wt.-4.0% by wt. | zinc |
| 0.1% by wt.-1.0% by wt. | impurities such as for example other metals, metal salts and non metals. |

One preferred composition of a magnesium alloy of the invention comprises or consists of:

| 80.0% by wt.-94.7% by wt. | magnesium |
|---|---|
| 5.0% by wt.-15.0% by wt. | dysprosium |
| 0.1% by wt.-2.0% by wt. | neodymium |
| 0.1% by wt.-2.0% by wt. | zinc |
| 0.1% by wt.-1.0% by wt. | impurities such as for example other metals, metal salts and non metals. |

One further, preferred composition of a magnesium alloy of the invention comprises or consists of:

| 81.7% by wt.-94.7% by wt. | magnesium |
|---|---|
| 5.0% by wt.-15.0% by wt. | dysprosium |
| 0.1% by wt.-2.0% by wt. | neodymium |
| 0.1% by wt.-0.3% by wt. | zirconium |
| 0.1% by wt.-1.0% by wt. | impurities such as for example other metals, metal salts and non metals. |

One further, preferred composition of a magnesium alloy of the invention comprises or consists of:

| 79.7% by wt.-94.6% by wt. | magnesium |
|---|---|
| 5.0% by wt.-15.0% by wt. | dysprosium |
| 0.1% by wt.-2.0% by wt. | neodymium |
| 0.1% by wt.-2.0% by wt. | zinc |
| 0.1% by wt.-0.3% by wt. | zirconium |
| 0.1% by wt.-1.0% by wt. | impurities such as for example other metals, metal salts and non metals. |

One further, preferred composition of a magnesium alloy of the invention comprises or consists of:

| 79.7% by wt.-94.6% by wt. | magnesium |
|---|---|
| 5.0% by wt.-15.0% by wt. | dysprosium |
| 0.1% by wt.-2.0% by wt. | europium |
| 0.1% by wt.-2.0% by wt. | zinc |
| 0.1% by wt.-0.3% by wt. | zirconium |
| 0.1% by wt.-1.0% by wt. | impurities such as for example other metals, metal salts and non metals. |

One further, preferred composition of a magnesium alloy of the invention comprises or consists of:

| 77.7% by wt.-94.5% by wt. | magnesium |
|---|---|
| 5.0% by wt.-15.0% by wt. | dysprosium |
| 0.1% by wt.-2.0% by wt. | europium |
| 0.1% by wt.-2.0% by wt. | neodymium |
| 0.1% by wt.-2.0% by wt. | zinc |
| 0.1% by wt.-0.3% by wt. | zirconium |
| 0.1% by wt.-1.0% by wt. | impurities such as for example other metals, metal salts and non metals. |

One further, preferred composition of a magnesium alloy of the invention comprises or consists of:

| 79.0% by wt.-94.75% by wt. | magnesium |
|---|---|
| 5.0% by wt.-15.0% by wt. | dysprosium |
| 0.2% by wt.-4.0% by wt. | europium |
| 0.05% by wt.-2.0% by wt. | zirconium |

One further, preferred composition of a magnesium alloy of the invention comprises or consists of:

| 88% by wt. | magnesium |
|---|---|
| 10% by wt. | dysprosium |
| 1% by wt. | europium |
| 1% by wt. | zirconium |

One further, preferred composition of a magnesium alloy of the invention comprises or consists of:

| 77.0% by wt.-94.75% by wt. | magnesium |
|---|---|
| 5.0% by wt.-15.0% by wt. | dysprosium |
| 0.2% by wt.-4.0% by wt. | europium |
| 0.05% by wt.-4.0% by wt. | zinc |

One further, preferred composition of a magnesium alloy of the invention comprises or consists of:

| 88% by wt. | magnesium |
|---|---|
| 10% by wt. | dysprosium |
| 1% by wt. | europium |
| 1% by wt. | zinc |

One further, preferred composition of a magnesium alloy of the invention comprises or consists of:

| 75.0% by wt.-94.7% by wt. | magnesium |
|---|---|
| 5.0% by wt.-15.0% by wt. | dysprosium |
| 0.2% by wt.-4.0% by wt. | europium |
| 0.05% by wt.-4.0% by wt. | zinc |
| 0.05% by wt.-2.0% by wt. | zirconium |

One further, preferred composition of a magnesium alloy of the invention comprises or consists of:

| | |
|---|---|
| 87% by wt. | magnesium |
| 10% by wt. | dysprosium |
| 1% by wt. | europium |
| 1% by wt. | zinc |
| 1% by wt. | zirconium |

One especially preferred composition of a magnesium alloy of the invention comprises or consists of:

| | |
|---|---|
| 87.8% by wt. | magnesium |
| 10.0% by wt. | dysprosium |
| 1.0% by wt. | neodymium |
| 1.0% by wt. | zinc |
| 0.2% by wt. | zirconium |

One further, especially preferred composition of a magnesium alloy of the invention comprises or consists of:

| | |
|---|---|
| 87.8% by wt. | magnesium |
| 10.0% by wt. | dysprosium |
| 1.0% by wt. | europium |
| 1.0% by wt. | zinc |
| 0.2% by wt. | zirconium |

One further, especially preferred composition of a magnesium alloy of the invention comprises or consists of:

| | |
|---|---|
| 86.8% by wt. | magnesium |
| 10.0% by wt. | dysprosium |
| 1.0% by wt. | neodymium |
| 1.0% by wt. | europium |
| 1.0% by wt. | zinc |
| 0.2% by wt. | zirconium |

All percentages by weight specified in this disclosure refer to the total weight of the corresponding alloy. Therefore it applies to all compositions, mentioned herein, that the sum of all components in total must add up to 100.00% by wt. That means, after addition of all listed components of the magnesium alloy, the difference to 100% by wt. is magnesium as the main component. In addition, these compositions can contain a very low amount of partially unavoidable, production-related impurities. It is preferred that these impurities are each ≤0.2% by wt., preferably ≤0.02% by wt., and especially preferred ≤250 ppm by wt. and in the sum of all impurities ≤0.4% by wt., preferably ≤0.05% by wt. and especially preferred ≤150 ppm.

It is in particular preferred, if the unavoidable impurities account for less than 0.1% by wt., preferred 0.05% by wt. and further preferred 0.01% by wt., further preferred below 150 ppm and especially preferred below 100 ppm. If the impurities are metals, metal salts, or metal carbides, metal nitrides, metal oxides, metal silicates, or metal silicides, it is preferred that such impurities are each present in amounts of below 300 ppm, preferred 200 ppm and further preferred below 150 ppm.

The term "impurities", as herein used, indicates all components of the alloy except magnesium, dysprosium, neodymium, europium, zinc, and zirconium regardless if these are explicitly listed or not.

Further the present invention comprises preferably magnesium alloys, which contain no additional components besides magnesium, dysprosium, neodymium, zinc, zirconium and unavoidable, production-related impurities. That is, it is preferred, if the components of the alloy, beside the basis magnesium, are selected from the following group consisting or comprising of: dysprosium, neodymium, europium, zinc, zirconium and unavoidable, production-related impurities. It is particularly preferred that the alloys of the present invention contain no yttrium. No yttrium means a maximum of 150 ppm yttrium. In vitro yttrium is less tolerable to cells than other rare earths such as dysprosium. In addition, the effectiveness of yttrium to improve the strength by solid solution- and precipitation-hardening, respectively, is clearly lower than that of other rare earths, such as dysprosium, because yttrium has a solubility in magnesium clearly lower than dysprosium (solubility in magnesium Y:12.47% by wt., Dy:25.34% by wt.). Free gadolinium ions are highly toxic. Because of the high toxicity of free gadolinium ions these are used in contrast agents only with chelating agents having high stability constants (e.g. the chelating agent DTPA). But today it is assumed that a release of highly toxic free gadolinium ions from contrast agents causes the development of nephrogenic systemic fibrosis in patients with severe renal insufficiency, dialysis patients and liver transplant patients. Lithium is used in form of specific salts as a medicament for psychic illnesses, especially for affective disorders. However, lithium has a narrow therapeutic index and even serum levels of 1.5 mmol/l can cause side effects. Within long-term treatment with lithium water and sodium loss (diabetes insipidus), hyperacidity of the blood (acidosis) and a lithium-nephropathy with a reduction in kidney function may occur. One of the problems here is that the $Li^+$ plasma level and thus the lithium effect is influenced by all substances and external circumstances with an effect on the $Na^+$ excretion. Therefore, a potential risk of unwanted side effects arises from the release of lithium ions.

Furthermore, it is therefore preferred, if the composition of the magnesium alloy contains no lithium and/or no gadolinium. These metals are preferably not included or only in small amounts of in total 0.01% by wt.-0.1% by wt., preferred in amounts of in total 0.001% by wt.-0.01% by wt. Further preferred Li and Gd are contained only as impurities in the ppm-range below 150 ppm, particularly preferred below 100 ppm.

If additional components besides magnesium, dysprosium, neodymium, europium, zinc and/or zirconium are contained in the alloy, these additional components are impurities such as other metals, metal salts, non-metals, carbon, sulfur, nitrogen, oxygen, silicon and/or hydrogen, which combined are present in small amounts of <0.6% by wt., preferably <0.5% by wt., more preferably <0.4% by wt., more preferably <0.3% by wt., more preferably <0.2% by wt., and especially preferably <0.1% by wt.

As "other metals", which may be present in the composition of the magnesium alloy according to the invention, the following are to be mentioned: sodium, potassium, calcium, scandium, titanium, vanadium, chromium, iron, cobalt, nickel, copper, gallium, niobium, molybdenum, technetium, ruthenium, rhodium, palladium, silver, indium, tin, promethium, tantalum, tungsten, rhenium, platinum, gold and lead. Except lanthanum, cerium, praseodymium and samarium which can be present in the alloy each up to the maximum of 0.3% by wt., preferred 0.2% by wt. and further preferred up to the maximum of 0.1% by wt., and the elements strontium, sodium, potassium, calcium, scandium, titanium, vanadium, chromium, cobalt, gallium, niobium, molybdenum, technetium, ruthenium, rhodium, palladium, silver, indium, tin, promethium, tantalum, tungsten, rhenium, platinum, gold and lead which in particular are present only as impurities in the ppm range and should each not exceed an amount of 500 ppm, preferred 400 ppm, further preferred 300 ppm, even further preferred 200 ppm and in particular preferred 150 ppm.

Furthermore, metal salts may be present in very small amounts in the alloy. Salts of Fe, Cu, Ni or Co may only be present in amounts up to 100 ppm preferably up to 50 ppm. The elements terbium, holmium, erbium, thulium, ytterbium, lutetium, beryllium, aluminium, manganese, copper, nickel, iron, lithium and gadolinium should preferably be contained in the alloy each in amounts less than 300 ppm, preferred 200 ppm, further preferred 150 ppm and particularly preferred each 100 ppm and combined not exceed an amount of 3000 ppm, preferred 2000 ppm, further preferred 1500 ppm and especially preferred each 1000 ppm.

Metal salts preferably contain at least one of the following metal ions: $Na^+$, $Mg^{2+}$, $K^+$, $Ca^{2+}$, $Sc^{3+}$ $Ti^{2+}$, $Ti^{4+}$, $V^{2+}$, $V^{3+}$, $V^{4+}$, $V^{5+}$, $Cr^{2+}$, $Cr^{3+}$, $Cr^{4+}$, $Cr^{6+}$, $Fe^{2+}$, $Fe^{3+}$, $Co^{2+}$, $Co^{3+}$, $Ni^{2+}$, $Cu^+$, $Cu^{2+}$, $Zn^{2+}$, $Zr^{2+}$, $Zr^{4+}$, $Nb^{2+}$, $Nb^{4+}$, $Nb^{5+}$, $MO^{4+}$, $MO^{8+}$, $Tc^{2+}$, $Tc^{3+}$, $Tc^{4+}$, $Tb^{5+}$, $Tc^{6+}$, $Tc^{7+}$, $Ru^{3+}$, $Ru^{4+}$, $Ru^{5+}$, $RU^{8+}$, $RU^{7+}$, $RU^{8+}$, $Rh^{3+}$, $Rb^{4+}$, $Pd^{2+}$, $Pd^{3+}$, $Ag^+$, $In^+$, $In^{3+}$, $Ta^{4+}$, $Ta^{5+}$ $W^{4+}$, $W^{6+}$, $Pt^{2+}$, $Pt^{3+}$, $Pt^{4+}$, $Pt^{5+}$, $Pt^{6+}$, $Au^+$, $Au^{3+}$, $Au^{5+}$, $Sn^{2+}$, $Sn^{4+}$, $Pb^{2+}$, $Pb^{4+}$, $La^{3+}$ $Ce^{3+}$, $Ce^{4+}$, $Gd^{3+}$, $Nd^{3+}$, $Pr^{3+}$, $Pr^{3+}$, $Pm^{3+}$, $Sm^{3+}$, $Eu^{2+}$, $Dy^{3+}$.

As Anions are used halogens such as $F^-$, $Cl^-$, $Br^-$, oxides and hydroxides such as $OH^-$, $O^{2-}$, sulfates, carbonates, oxalates, phosphates such as $HSO_4^-$, $SO_4^{2-}$, $HCO_3^-$, $CO_3^{2-}$, $HC_2O_4^-$, $C_2O_4^{2-}$, $H_2PO_4$, $HPO_4^{2-}$, $PO_4^{3-}$.

The magnesium alloys according to the present invention are in particular suitable for the production of absorbable or degradable endoprostheses and especially vascular implants or stents, respectively.

Furthermore, the present invention, thus, refers to an absorbable stent or an absorbable, vascular implant consisting of any magnesium alloy disclosed herein. The absorbable stent is preferably a stent for blood vessels, urinary tracts, respiratory tracts, biliary tracts or the digestive tract. In turn, among these stents are the vascular implants or stents for blood vessels or more generally for the cardiovascular system are preferred.

The term "absorbable", as used herein, means that the implant slowly dissolves in a human or animal organism over a certain time and at some point only its degradation products are present in the body in a dissolved form. At this point in time solid components or fragments of the implant do not exist anymore. The degradation products should be substantially harmless in physiological terms and lead to ions or molecules which occur in the organism anyway, or can be degraded by the organism to harmless substances, or can be excreted.

The stents or vascular implants are preferably cut by laser from a tube which consists of a magnesium alloy according to the invention. The stents of the present invention are absorbed under physiological conditions within a period of time of 8 to 50 weeks, preferably from 10 to 30 weeks.

The terms "absorbable" or "degradable" or "biodegradable" or "biologically degradable" thus refer to the fact that the human or animal body is capable of decomposing the stent or the vascular implants within a certain period of time, so that atoms, ions or molecules are present, which can be present in dissolved state in the blood or in other bodily fluids.

Stents as used herein are grid-shaped or net-shaped endoprostheses which are implanted into a hollow organ or a body cavity, to keep it open. A stent is not a massive tube, but a mesh network. If one considers, for example, a vascular stent, it is cut out, e.g. using a laser, of a massive tube, so that single struts as thin as possible are resulting, which are connected to each other. The arrangement and formation of the struts and nodes is called the stent design.

When cutting a stent, areas between the individual struts are cut out. A stent or a vascular implant therefore has a plurality of solid scaffolding components (e.g. struts in the form of rings, spirals, waves and wires), which altogether form the endoprosthesis or the stent, as well as a plurality of interstices between these solid components. Within the common embodiment of endoprostheses or stents the struts merge in nodes. However, there are also embodiments of endoprostheses, where no or almost no nodes are present and the struts for example have the form of rings or spirals. Preferably the stents are self-expanding or balloon expandable stents, which are pushed by a catheter to the diseased area or to the area to be treated, where the stents are expanded to their defined nominal diameter.

The vascular implants or stents are cut using lasers from tubes which consist of an alloy according to the present invention. The tubes are obtained by transformation of wires from the alloys of the invention. The alloys of the invention are preferably produced in the so-called permanent mold direct chill casting ("Tütengußverfahren"). In this method, the components of the magnesium alloys are melted in a smoothed steel crucible under an inert gas atmosphere at a molten bath temperature of 660 to 740° C. The melt is stirred until complete mixing has taken place and then transferred into a thin-walled coquille which was preheated to a temperature of 600° C. and kept for one hour at a temperature of about 700° C. Thereafter, the coquille is cooled in a water bath at a temperature of 15-20° C. The obtained pins are then heated before extrusion to a temperature of 250-500° C. and kept at this temperature for 3-6 hours. Extrusion and the cooling of the extruded billet to room temperature follow.

The present invention refers therefore to inventive alloys obtainable by permanent mold direct chill casting ("Tütengußverfahren"). Particularly preferred is a magnesium alloy obtained using permanent mold direct chill casting composed of the following components based on the total weight of the alloy:

| | |
|---|---|
| 80.4% by wt.-94.6% by wt. | magnesium |
| 5.0% by wt.-15.0% by wt. | dysprosium |
| 0.1% by wt.-2.0% by wt. | neodymium and/or europium |
| 0.1% by wt.-2.0% by wt. | zinc |
| 0.1% by wt.-0.3% by wt. | zirconium | and impurities such as for example other metals, metal salts and non metals in the herein disclosed amounts, wherein the alloy contains no yttrium and no gadolinium.

The present invention further refers to all further magnesium alloys with one of the compositions disclosed herein obtained using permanent mold direct chill casting. Therefore the disclosed, preferred ranges of the single alloying components are also valid for the magnesium alloys obtained after permanent mold direct chill casting.

Furthermore the present invention refers to wires which are preferably produced by extrusion of alloys according to the invention obtained after permanent mold direct chill casting. The preferred ranges of the single alloying components disclosed herein refer also to wires of magnesium alloys obtained using the permanent mold direct chill casting. The present invention, thus, comprises in particular wires obtainable from a magnesium alloy obtained after permanent mold direct chill casting comprising the following components based on the total weight of the alloy:

| | |
|---|---|
| 80.4% by wt.-94.6% by wt. | magnesium |
| 5.0% by wt.-15.0% by wt. | dysprosium |
| 0.1% by wt.-2.0% by wt. | neodymium and/or europium |
| 0.1% by wt.-2.0% by wt. | zinc |
| 0.1% by wt.-0.3% by wt. | zirconium | and impurities such as for example other metals, metal salts and non metals in the amounts herein disclosed, wherein the alloy contains no yttrium and no gadolinium and wherein the wires were obtained by extrusion.

Furthermore the present invention refers to tubes which are preferably produced from wires obtainable by extrusion, which consist of alloys according to the invention obtained after permanent mold direct chill casting. The preferred ranges of the single alloying components disclosed herein are also valid for tubes made from wires consisting of magnesium alloys obtained using the permanent mold direct chill casting. The present invention, thus, comprises in particular tubes obtainable from a magnesium alloy obtained after permanent mold direct chill casting comprising the following components based on the total weight of the alloy:

| | |
|---|---|
| 80.4% by wt.-94.6% by wt. | magnesium |
| 5.0% by wt.-15.0% by wt. | dysprosium |
| 0.1% by wt.-2.0% by wt. | neodymium and/or europium |
| 0.1% by wt.-2.0% by wt. | zinc |
| 0.1% by wt.-0.3% by wt. | zirconium | and impurities such as for example other metals, metal salts and non metals in the amounts herein disclosed, wherein the alloy contains no yttrium and no gadolinium and wherein the tubes are obtainable from wires which were obtained by extrusion.

Furthermore, the present invention refers to stents, which are cut from the tubes, wherein the tubes are made of wires preferably obtainable by extrusion, wherein the wires consist of the alloys according to the invention obtainable after permanent mold direct chill casting. The preferred ranges of the single alloying components disclosed herein are also valid for stents made of tubes, which were again formed of wires consisting of magnesium alloys obtained after permanent mold direct chill casting.

The present invention refers further to a method for the production of absorbable stents, comprising the following steps:
a) Providing an alloy according to the invention obtainable after permanent mold direct chill casting
b) Production of a wire made of the alloy obtained after step a) by extrusion,
c) Production of a tube made of the wire obtained after step b), and
d) Cutting of stents from the tube obtained after step c).

The invention comprises also absorbable stents obtained according to the method above. In step d) a laser is preferably used to cut the stents from the tube obtained according to step c). To obtain a magnesium alloy according to the invention after permanent mold direct chill casting further steps may be carried out prior to step a). In these steps, the components of the magnesium alloys are melted in a smoothed steel crucible by sequential addition in form of pure elements or as master alloys at a molten bath temperature of 660-740° C. in a smoothed steel crucible. Virtually any nickel-free steel can be used as material for the crucible. Graphite would be another possibility. All melting operations are carried out under inert gas. After addition of the alloying elements the melt is stirred mechanically. In a next step, the melt is transferred into a thin-walled coquille, which was preheated to a temperature of 600° C. In a last step, the coquille is immersed in a water bath which has a temperature of 15-20° C.

In an animal experiment study (see example 7) on effectiveness and harmlessness of stents made of magnesium alloys according to the invention it could be shown that the stents or vascular implants according to the invention made of the magnesium alloys disclosed herein can be crimped on a balloon without problems. The implantation of the stents was made without occurrence of known complications, like stent malapposition, thromboses or dissection. Already after 4 weeks, a complete re-endothelialization of the stented vessel segments has been observed. This indicates that now excessive inflammation reactions occurred and the magnesium alloys according to the inventions have caused no intolerance reactions in the tissue of the vessel. The rate of restenosis was in the range of values of common bare metal stents (BMS) of the prior art, respectively in the range of the "worser" drug-eluting stents (DES) (see figures to the talk of R. A. Costa; given within the Euro-PCR, Paris, May 2011).

DESCRIPTION OF THE FIGURES

FIG. 6A has been taken without an X-ray contrast agent, after the catheter has been advanced up to the appropriate coronary artery. The two arrows point to the radio-opaque markers distal and proximal of the still folded catheter balloon on which the stent is mounted. FIG. 6B has been taken with X-ray contrast agent during the dilatation of the catheter balloon to expand and place the stent. The two arrows mark the ends of the catheter balloon. The catheter balloon occludes the vessel, so that the X-ray contrast agent cannot penetrate into the underlying part of the vessel. The stent balloon to artery ratio was 1.2 to 1. FIG. 6C has been taken without X-ray contrast agent after the catheter with the balloon has been withdrawn from the vessel. Thereby the stent remains in the vessel, but is not visible on the image, because the magnesium alloy of the invention is not radio-opaque.

FIG. 6D has been taken with X-ray contrast medium after the catheter with the balloon has been withdrawn from the vessel. Thereby the stent remains in the vessel. The arrows point to the ends of the stent. In the region of the stent slightly more contrast agent accumulates. But the stent itself is not recognizable.

EXAMPLES

Example 1

Production of the Alloys

Figure 1:
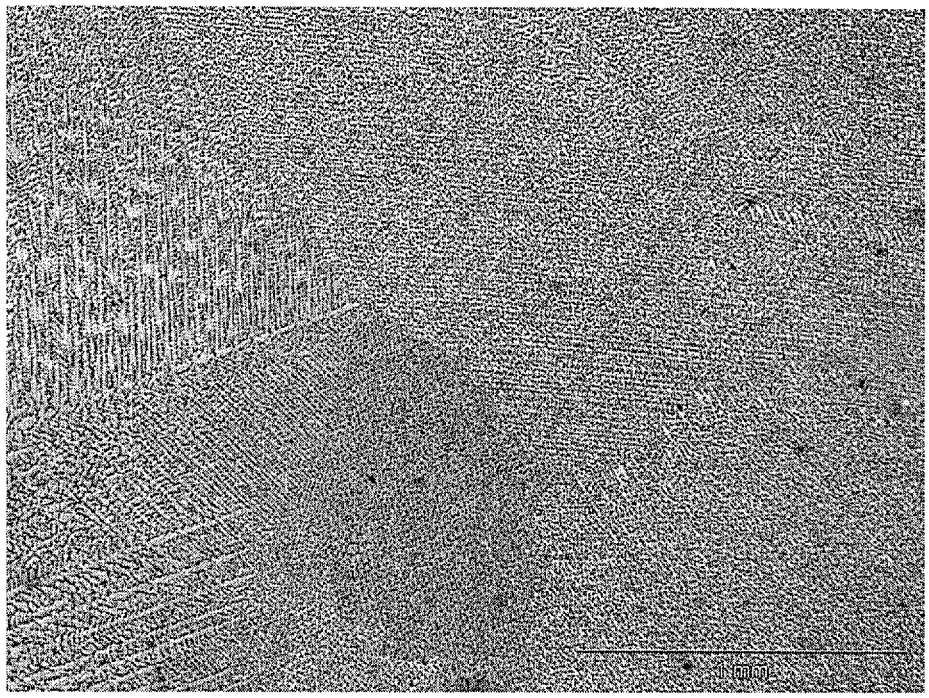
FIG. 1: shows an image for determining the grain size of a magnesium alloy with 10% by wt. Dy and 1% by wt. Nd.
Figure 2:
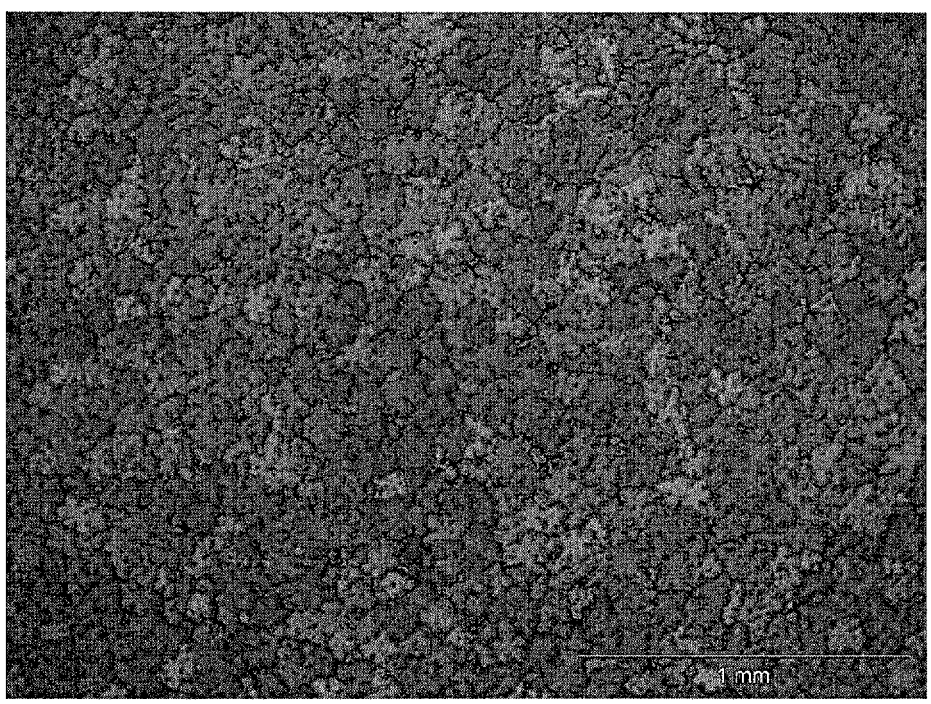
FIG. 2: shows an image for determining the grain size of a magnesium alloy with 10% by wt. Dy, 1% by wt. Nd and 0.6% by wt. Zr.
Figure 3:
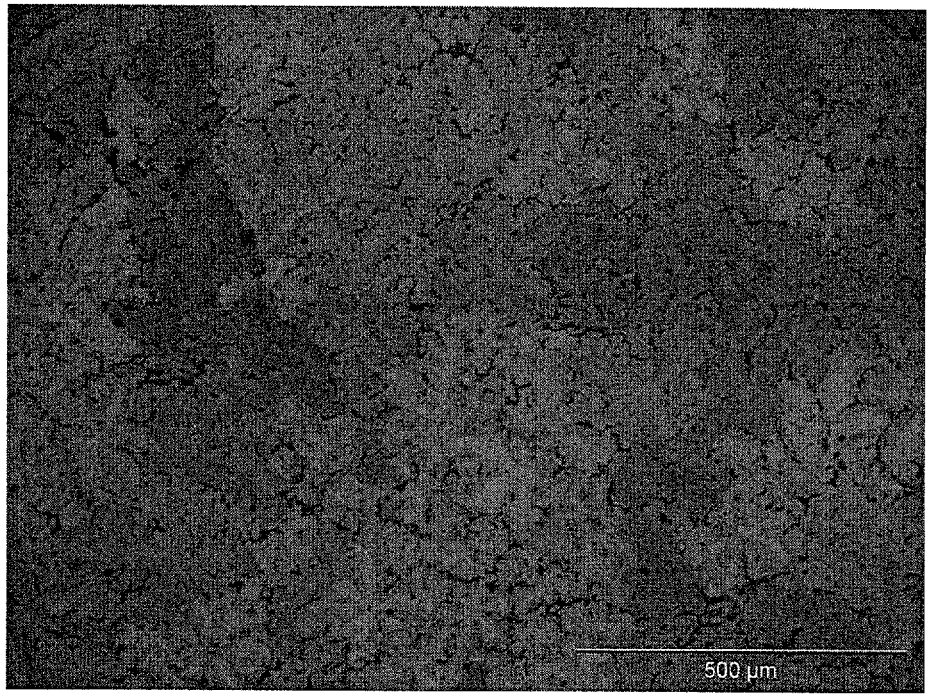
FIG. 3: shows an image for determining the grain size of a magnesium alloy with 10% by wt. Dy, 1% by wt. Nd and 0.2% by wt. Zr. The grain size is 102 µm.
Figure 4:
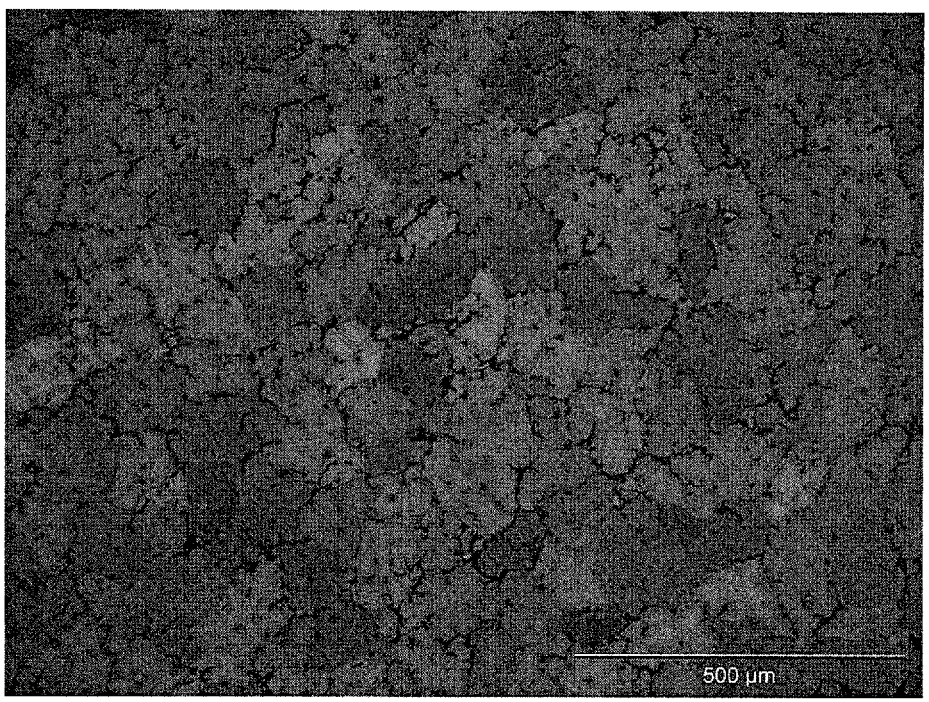
FIG. 4: shows an image for determining the grain size of a magnesium alloy with 10% by wt. Dy, 1% by wt. Nd and 0.4% by wt. Zr. The grain size is 68 µm.
Figure 5:
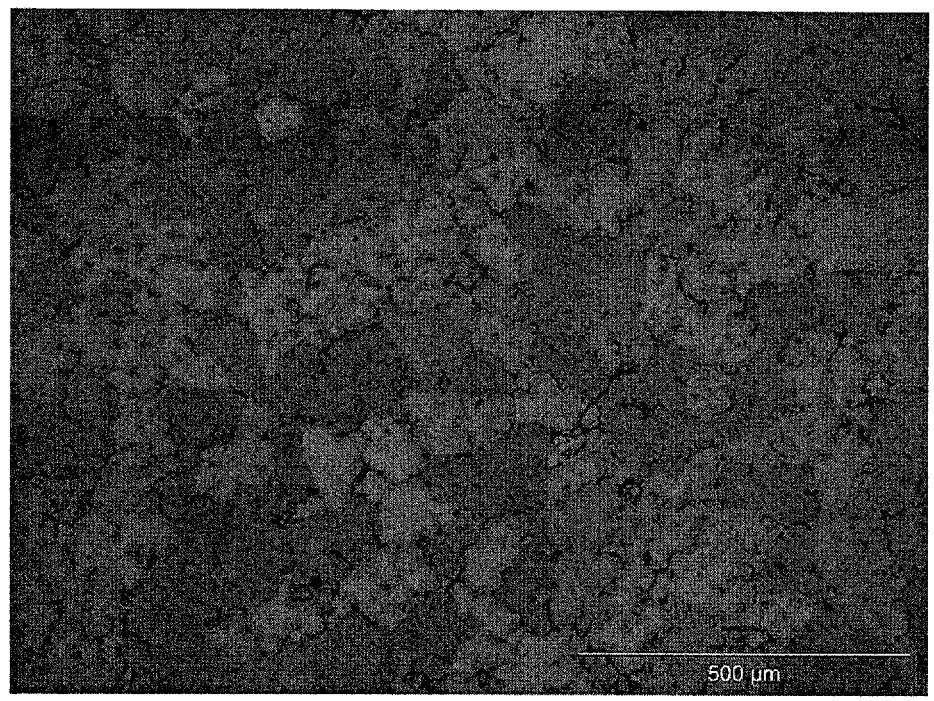
FIG. 5: shows an image for determining the grain size of a magnesium alloy with 10% by wt. Dy, 1% by wt. Nd and 0.6% by wt. Zr. The grain size is 64 µm.
Figure 6:
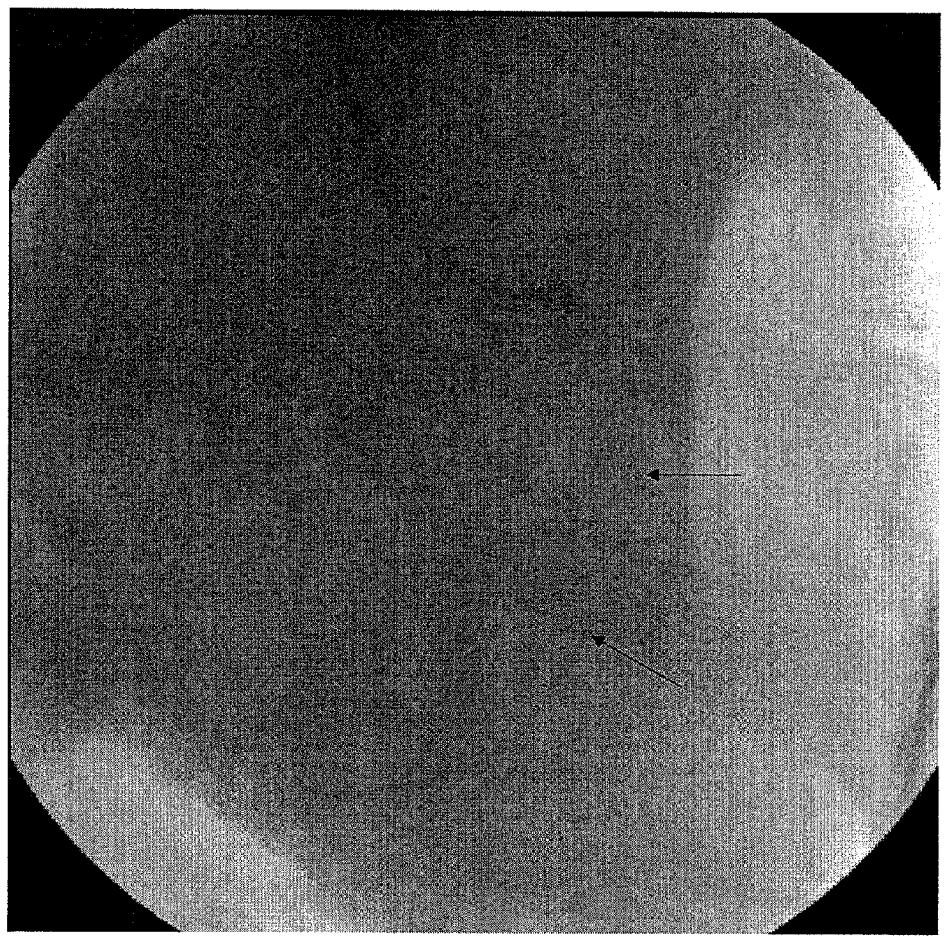
FIG. 6: shows 4 snapshots during the balloon angioplasty for implantation of an uncoated stent of the invention in a pig (see Example 8).
Figure 6:
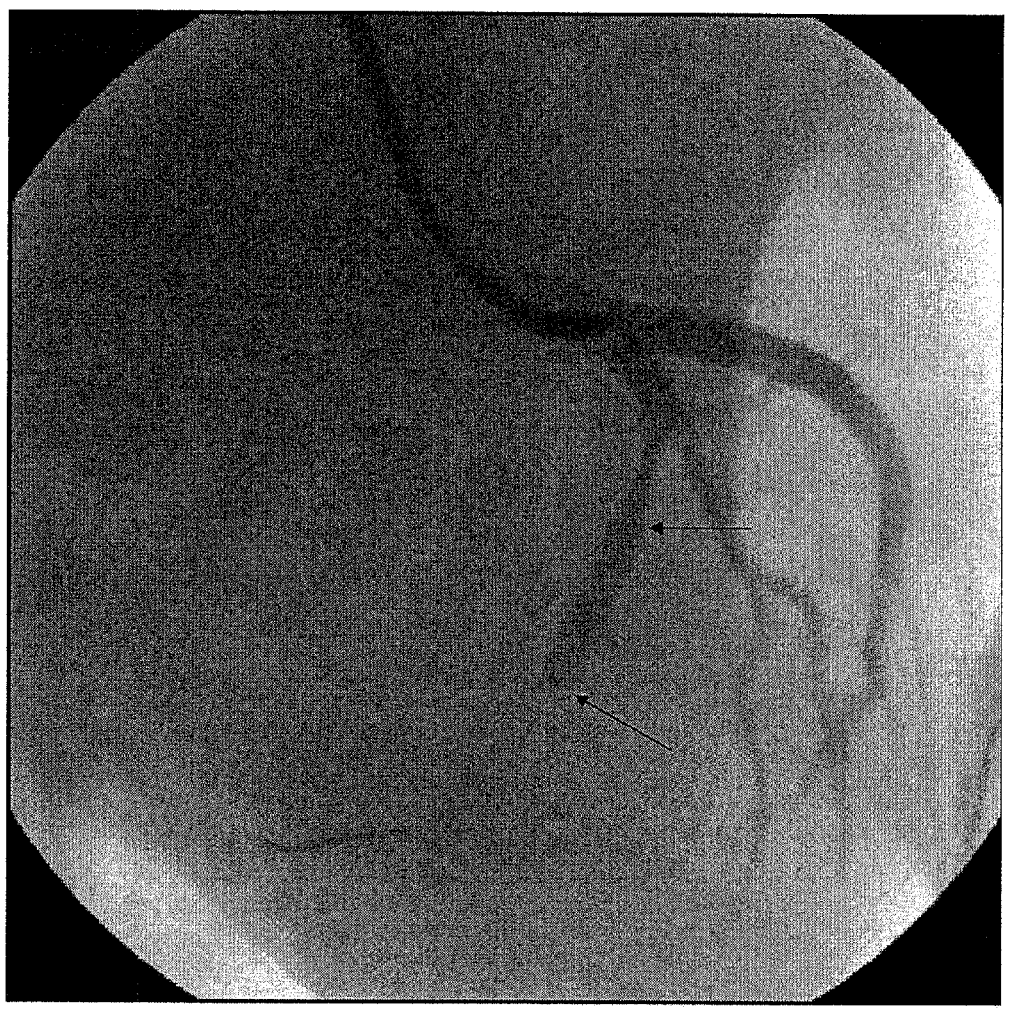
Figure 6:
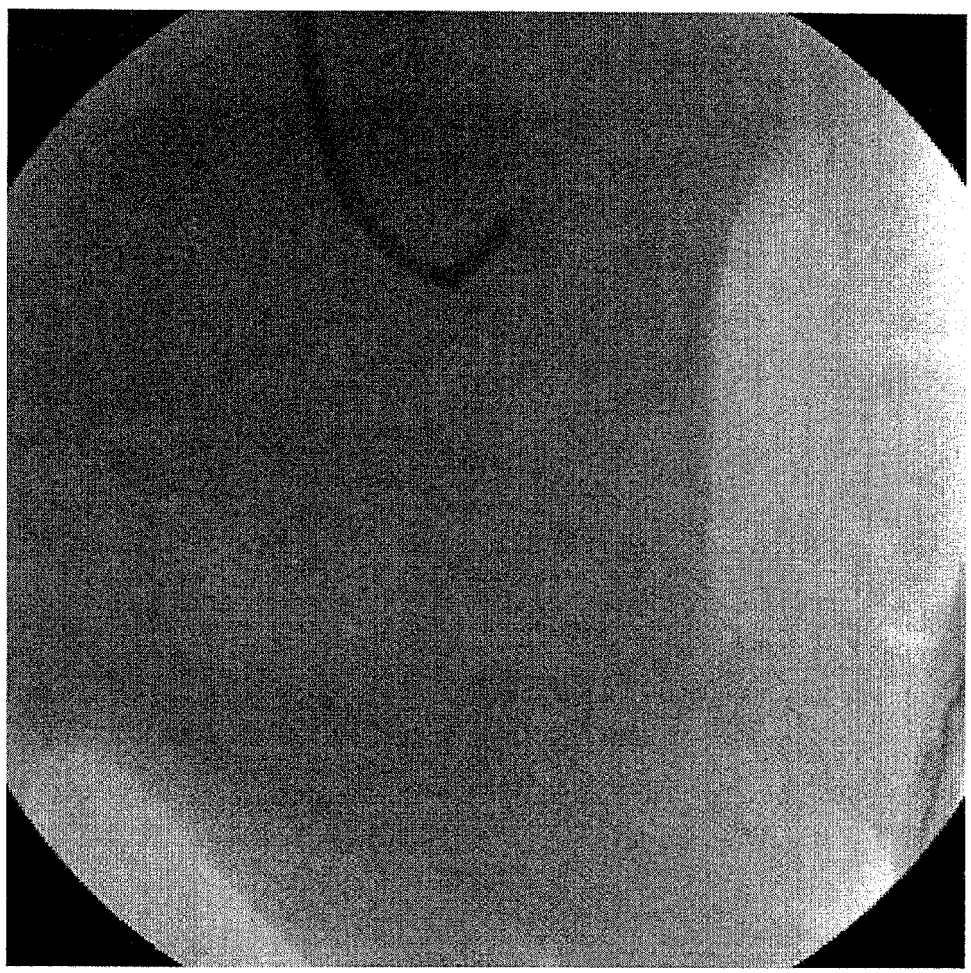
Figure 6:
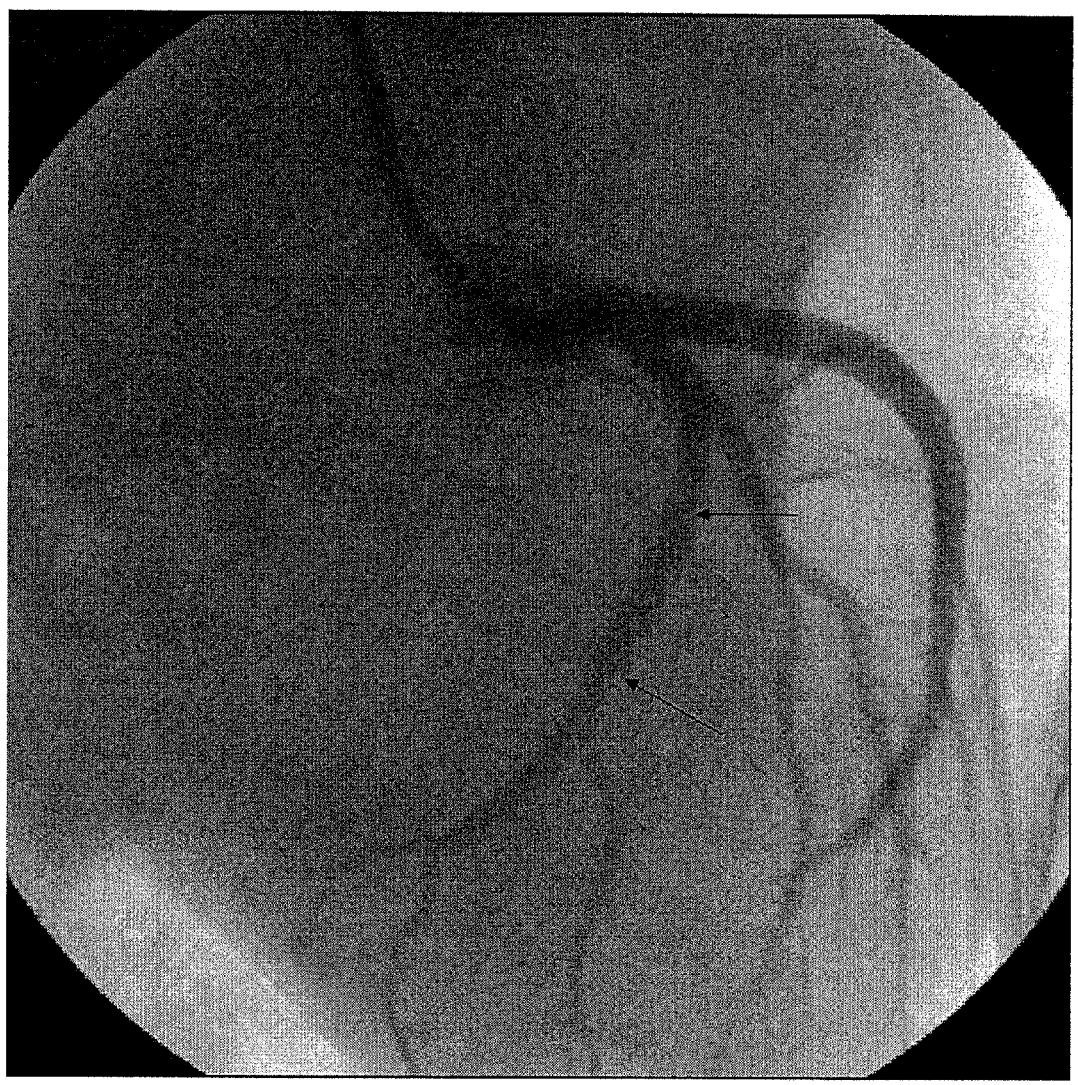

The alloys were produced in the so-called permanent mold direct chill casting ("Tütengußverfahren"). This method is used to produce precursors for the subsequent extrusion and is characterized in that material with a homogeneous microstructure and a homogeneous distribution of alloying elements in the ingot can be produced. Therefore it is exceptionally suitable to produce smaller quantities of high quality pins for the metal forming.

With this method, the magnesium alloys (L1, L2, . . . , L34) are melted in a smoothed steel crucible. As a crucible material virtually any nickel-free steel may be used. Graphite would be another possibility. All melting operations are carried out under inert gas. The temperatures of the molten bath are in the range of 660-740° C. Upon reaching the temperature of the molten bath, the alloying elements in the form of pure elements or as master alloys were added. After addition of the alloying elements the melt was stirred mechanically. The stirring time is dependent on how long it takes for the elements or master alloys to completely dissolve in the melt. After this preparation, the melt was transferred to a thin-walled coquille which was preheated to a temperature of 600° C. After a period of about 60 minutes, the coquille was immersed in a water bath having a temperature of 15-20° C. Upon immersing the coquille completely solidified.

Prior to extrusion the surface of the cast part was adjusted to the diameter of the recipient of the extrusion press. In addition, prior to extrusion the casting pin has been heated to a temperature of 250-500° C. and kept for 3-6 hours at this temperature to dissolve intermetallic phases or to homogenize segregations. Subsequent to this extrusion followed and the billet produced in this manner was cooled in air to room temperature. Wires were obtained which were then transformed into tubes.

The following alloys were prepared:

| Alloy L1: | |
|---|---|
| 87.8% by wt. | magnesium |
| 10.0% by wt. | dysprosium |
| 1.0% by wt. | neodymium |
| 1.0% by wt. | zinc |
| 0.2% by wt. | Impurities comprising Si, Ni, Fe, Cu and other metals and non-metals. |
| Alloy L2: | |
| 88.6% by wt. | magnesium |
| 10.0% by wt. | dysprosium |
| 1.0% by wt. | neodymium |
| 0.2% by wt. | zirconium |
| 0.2% by wt. | Impurities comprising Si, Ni, Fe, Cu and other metals and non-metals. |
| Alloy L3: | |
| 87.6% by wt. | magnesium |
| 10.0% by wt. | dysprosium |
| 1.0% by wt. | neodymium |
| 1.0% by wt. | zinc |
| 0.2% by wt. | zirconium |
| 0.2% by wt. | Impurities comprising Si, Ni, Fe, Cu and other metals and non-metals. |
| Alloy L4: | |
| 89.7% by wt. | magnesium |
| 6.0% by wt. | dysprosium |
| 2.0% by wt. | neodymium |
| 2.0% by wt. | zinc |
| 0.3% by wt. | Impurities comprising Si, Ni, Fe, Cu and other metals and non-metals. |
| Alloy L5: | |
| 90.7% by wt. | magnesium |
| 5.5% by wt. | dysprosium |
| 3.0% by wt. | neodymium |
| 0.5% by wt. | zirconium |
| 0.3% by wt. | Impurities comprising Si, Ni, Fe, Cu and other metals and non-metals. |
| Alloy L6: | |
| 87.4% by wt. | magnesium |
| 8.0% by wt. | dysprosium |
| 2.2% by wt. | neodymium |
| 1.8% by wt. | zinc |
| 0.3% by wt. | zirconium |
| 0.3% by wt. | Impurities comprising Si, Ni, Fe, Cu and other metals and non-metals. |
| Alloy L7: | |
| 82.7% by wt. | magnesium |
| 12.0% by wt. | dysprosium |
| 2.5% by wt. | neodymium |
| 2.5% by wt. | zinc |
| 0.3% by wt. | Impurities comprising Si, Ni, Fe, Cu and other metals and non-metals. |
| Alloy L8: | |
| 74.2% by wt. | magnesium |
| 22.5% by wt. | dysprosium |
| 2.6% by wt. | neodymium |
| 0.4% by wt. | zirconium |
| 0.3% by wt. | Impurities comprising Si, Ni, Fe, Cu and other metals and non-metals. |
| Alloy L9: | |
| 83.1% by wt. | magnesium |
| 15.2% by wt. | dysprosium |
| 1.2% by wt. | neodymium |
| 0.2% by wt. | zirconium |
| 0.3% by wt. | Impurities comprising Si, Ni, Fe, Cu and other metals and non-metals. |
| Alloy L10: | |
| 88.9% by wt. | magnesium |
| 8.0% by wt. | dysprosium |
| 1.4% by wt. | neodymium |
| 1.2% by wt. | zinc |
| 0.2% by wt. | zirconium |
| 0.3% by wt. | Impurities comprising Si, Ni, Fe, Cu and other metals and non-metals. |
| Alloy L11: | |
| 90.6% by wt. | magnesium |
| 8.0% by wt. | dysprosium |
| 1.0% by wt. | neodymium |
| 0.2% by wt. | zinc |
| 0.2% by wt. | zirconium |

-continued

Alloy L12:
| | |
|---|---|
| 89.3% by wt. | magnesium |
| 8.0% by wt. | dysprosium |
| 1.0% by wt. | neodymium |
| 1.0% by wt. | europium |
| 0.5% by wt. | zinc |
| 0.2% by wt. | zirconium |

Alloy L13:
| | |
|---|---|
| 86.0% by wt. | magnesium |
| 12.0% by wt. | dysprosium |
| 1.0% by wt. | neodymium |
| 0.8% by wt. | zinc |
| 0.2% by wt. | zirconium |

Alloy L14:
| | |
|---|---|
| 90.1% by wt. | magnesium |
| 6.0% by wt. | dysprosium |
| 1.0% by wt. | neodymium |
| 1.0% by wt. | europium |
| 1.5% by wt. | zinc |
| 0.4% by wt. | zirconium |

Alloy L15:
| | |
|---|---|
| 86.8% by wt. | magnesium |
| 10.0% by wt. | dysprosium |
| 1.0% by wt. | neodymium |
| 1.0% by wt. | europium |
| 1.0% by wt. | zinc |
| 0.2% by wt. | zirconium |

Alloy L16:
| | |
|---|---|
| 82.8% by wt. | magnesium |
| 14.0% by wt. | dysprosium |
| 0.5% by wt. | neodymium |
| 0.5% by wt. | europium |
| 2.0% by wt. | zinc |
| 0.2% by wt. | zirconium |

Alloy L17:
| | |
|---|---|
| 87.3% by wt. | magnesium |
| 10.0% by wt. | dysprosium |
| 1.5% by wt. | neodymium |
| 1.0% by wt. | zinc |
| 0.2% by wt. | zirconium |

Alloy L18:
| | |
|---|---|
| 87.45% by wt. | magnesium |
| 10.0% by wt. | dysprosium |
| 1.5% by wt. | neodymium |
| 1.0% by wt. | zinc |
| 0.05% by wt. | iron |

Alloy L19:
| | |
|---|---|
| 83.1% by wt. | magnesium |
| 15.0% by wt. | dysprosium |
| 0.9% by wt. | neodymium |
| 1.0% by wt. | zirconium |

Alloy L20:
| | |
|---|---|
| 95.0% by wt. | magnesium |
| 4.5% by wt. | dysprosium |
| 0.5% by wt. | neodymium |

Alloy L21:
| | |
|---|---|
| 73.7% by wt. | magnesium |
| 20.0% by wt. | dysprosium |
| 5.0% by wt. | neodymium |
| 1.0% by wt. | zinc |
| 0.3% by wt. | zirconium |

Alloy L22:
| | |
|---|---|
| 87.25% by wt. | magnesium |
| 10.0% by wt. | dysprosium |
| 1.5% by wt. | neodymium |
| 1.0% by wt. | zinc |
| 0.05% by wt. | iron |
| 0.2% by wt. | zirconium |

Alloy L23:
| | |
|---|---|
| 85.8% by wt. | magnesium |
| 12.0% by wt. | dysprosium |
| 1.0% by wt. | neodymium |
| 1.0% by wt. | zinc |
| 0.2% by wt. | zirconium |

Alloy L24:
| | |
|---|---|
| 82.1% by wt. | magnesium |
| 15.0% by wt. | dysprosium |
| 0.9% by wt. | neodymium |
| 1.0% by wt. | zinc |
| 1.0% by wt. | zirconium |

Alloy L25:
| | |
|---|---|
| 79.1% by wt. | magnesium |
| 20.0% by wt. | yttrium |
| 0.9% by wt. | europium |

Alloy L26:
| | |
|---|---|
| 92.5% by wt. | magnesium |
| 5.0% by wt. | dysprosium |
| 2.5% by wt. | europium |

Alloy L27:
| | |
|---|---|
| 82.1% by wt. | magnesium |
| 15.5% by wt. | dysprosium |
| 1.2% by wt. | neodymium |
| 1.0% by wt. | zinc |
| 0.2% by wt. | zirconium |
| 0.001% by wt. | Impurities comprising Si, Ni, Fe, Cu and other metals and non-metals. |

Alloy L28:
| | |
|---|---|
| 72.0% by wt. | magnesium |
| 20.0% by wt. | gadolinium |
| 5.0% by wt. | neodymium |
| 1.0% by wt. | zinc |
| 2.0% by wt. | zirconium |

Alloy L29:
| | |
|---|---|
| 88.8% by wt. | magnesium |
| 6.0% by wt. | dysprosium |
| 4.0% by wt. | europium |
| 1.0% by wt. | zinc |
| 0.2% by wt. | zirconium |

Alloy L30:
| | |
|---|---|
| 89.8% by wt. | magnesium |
| 8.0% by wt. | dysprosium |
| 1.0% by wt. | europium |
| 1.0% by wt. | zinc |
| 0.2% by wt. | zirconium |

Alloy L31:
| | |
|---|---|
| 73.2% by wt. | magnesium |
| 25.0% by wt. | dysprosium |
| 0.4% by wt. | neodymium |
| 1.4% by wt. | europium |

Alloy L32:
| | |
|---|---|
| 87.4% by wt. | magnesium |
| 10.0% by wt. | dysprosium |
| 1.0% by wt. | europium |
| 0.5% by wt. | neodymium |
| 1.0% by wt. | zinc |
| 0.1% by wt. | zirconium |

Alloy L33:
| | |
|---|---|
| 87.0% by wt. | magnesium |
| 10.0% by wt. | dysprosium |
| 0.3% by wt. | europium |
| 1.5% by wt. | neodymium |
| 1.0% by wt. | zinc |
| 0.2% by wt. | zirconium |

-continued

Alloy L34:

| | |
|---|---|
| 86.0% by wt. | magnesium |
| 12.0% by wt. | dysprosium |
| 1.0% by wt. | europium |
| 0.8% by wt. | zinc |
| 0.2% by wt. | zirconium |

Example 2

Tube Production

From the alloys L1 to L10 extruded wires were prepared according to Example 1. In these extruded wires, a precision drill-hole is introduced in the longitudinal direction, which already co-determines the wall thickness of the later stents. Through several forming steps, a tube of predetermined diameter and certain wall thickness is made. Between the individual forming steps repeating heat treatment take place.

Example 3

Stent Production

A tube manufactured according to Example 2 is fixed into an adapter in the laser machine. A pulsed solid-state laser (FKL) cuts the contours of the stent design out of the tube. The laser cutting is performed under an inert gas atmosphere.

The stent design is stored in a NC program (numerical control). This provides the laser the traverse path (cutting pattern), after which the tube is structured. By the laser beam cutting burr formation occurs, especially on the inside of the tube, along the entire cutting contour. This can cause that remain in the contour after the end of the cutting process. The off-cuts and cut-outs will be mechanically removed and the stent is cleaned from manufacturing residues. In a first optical visual control an inspection of the cutting contour is performed.

In the following, the stent is electrochemically polished. The stent is anodically connected and immersed in an acid bath. Via a cathode fixed in the bath, an electric circuit is closed. The electric circuit is maintained for several minutes. The electropolishing is an inverted galvanic process where material is removed in a controlled manner from the surface of the anodically connected component. Due to the method removal takes preferably place at sharp corners and edges. The stent obtains a smooth surface and rounded edges along the contours. After polishing, the stent is cleaned and freed from acid residues. During the final cleaning all still remaining manufacturing residues are removed from the stent surface. In a last optical visual control the stent geometry is measured and the surface is tested on cleanliness.

Example 4

Determination of Grain Size

The counting of the grain size was made using linear intercept method. Grains which are only half cut at the end of the line were here counted as half grains. The magnification was selected such that at least 50 grains were cut by the grid. At least 5 sites with a total of at least 250 points of intersection were evaluated on the sample.

Example 5

Determination of Corrosion

Figure 7:
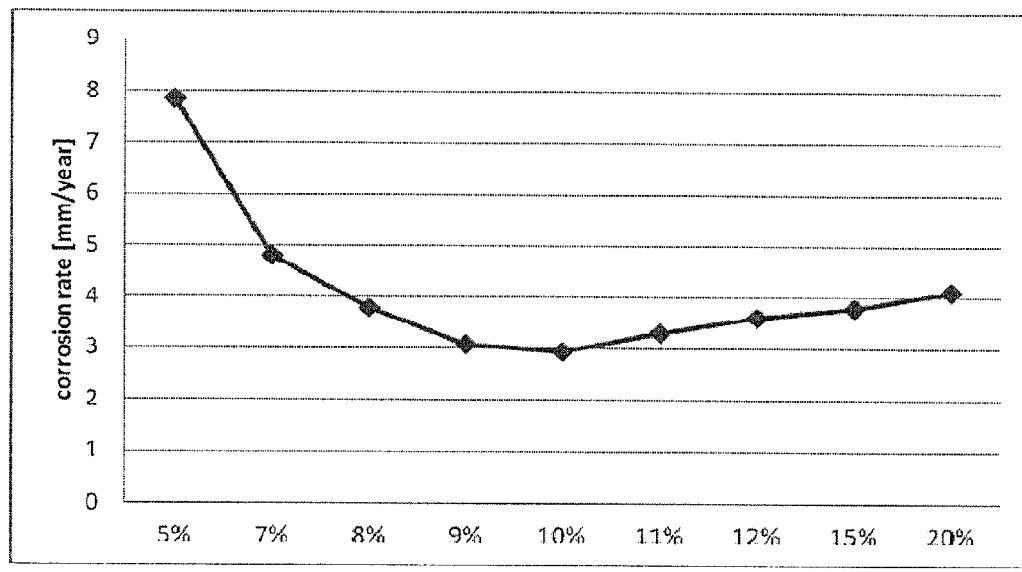
FIG. 7: shows a graphic representation of the results of the corrosion tests with binary magnesium alloys containing between 5 and 20% dysprosium and magnesium as balance. The corrosion was measured in 0.9% saline solution in a eudiometer. The data in % refer to the content of dysprosium in % by weight.
Figure 8:
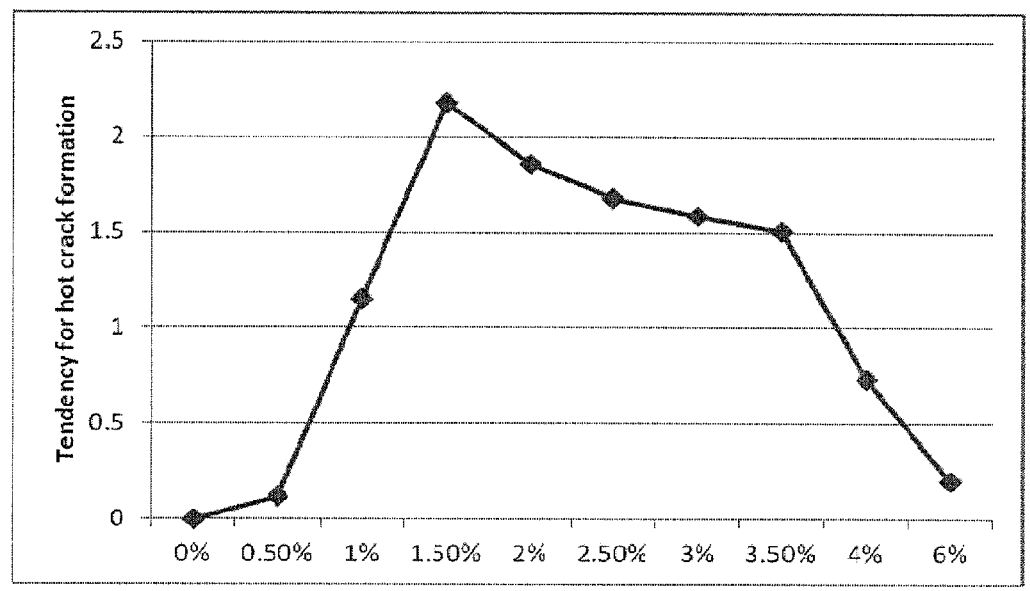
FIG. 8: shows a graphic representation of the dependence of the tendency for hot crack formation in connection with the amount of zinc in the alloy. Magnesium alloys according to the invention containing 10% dysprosium, 1.0% by weight neodymium, increasing % by weight zinc, 0.2% by weight zirconium and the balance of magnesium were tested. The data in % refer to the content of zinc in % by weight.

At room temperature, the corrosion rates of various alloys were determined for a period of 3 days in a physiological saline solution (see Table 1). An alloy was tested containing 90.8% by wt. Mg, 8% by wt. Dy, 1% by wt. Nd and 0.2% by wt. Zr, an alloy containing 89.8% by wt. Mg, 8% by wt. Dy, 1% by wt. Nd, 1% by wt. Eu and 0.2% by wt. Zr, an alloy containing 86.8% by wt. Mg, 12% by wt. Dy, 1% by wt. Nd, and 0.2% by wt. Zr, and an alloy containing 87.8% by wt. Mg, 10% by wt. Dy, 1% by wt. Nd, 1% by wt. Eu and 0.2% by wt. Zr. In addition alloys containing 1.0% by wt. neodymium, 1.0% by wt. zinc, 0.2% by wt. zirconium, between 5 and 20% dysprosium and the balance magnesium (see FIG. 7) were tested. Corrosion products were removed by immersing the samples in chromic acid (180 g/L) for 20 min at room temperature. The average corrosion rate was calculated in mm per year by the following equation:

$$CR = \frac{8.76 \times 10^4 \times \Delta g}{A \cdot t \cdot \rho}$$

TABLE 1

Corrosion rate of alloys of the invention, measured over 3 days at room temperature, and in 0.9% NaCl, the specification of the components of the alloy are in % by weight and Mg as major component adds always up to 100% of the alloy. The alloys were tested after casting, without heat treatment, the average values and standard deviations of the various alloys are listed.

| No. | Composition | Corrosion rate (mm/year) |
|---|---|---|
| L11 | Mg8Dy1Nd0.2Zn0.2Zr | 9.25 ± 0.38 |
| L15 | Mg10Dy1Nd1Eu1Zn0.2Zr | 0.81 ± 0.06 |
| L23 | Mg12Dy1Nd1Zn0.2Zr | 2.94 ± 1.88 |
| L16 | Mg8Dy1Nd1Eu1Zn0.1Zr | 4.9 ± 1.62 |
| L14 | Mg6Dy1Nd1Eu1.5Zn0.4Zr | 9.56 ± 0.29 |
| L16 | Mg14Dy0.5Nd0.5Eu2Zn0.2Zr | 1.25 ± 0.12 |
| L18 | Mg10Dy1.5Nd1Zn0.05Fe | 12.41 ± 2.16 |
| L20 | Mg4.5Dy0.5Nd | 25.56 ± 2.34 |
| L24 | Mg15Dy0.9Nd1Zr1Zn | 2.98 ± 1.78 |
| L25 | Mg20Y0.9Eu | 44.71 ± 3.22 |
| L28 | Mg20Gd5Nd1Zn2Zr | 38.96 ± 1.34 |
| L30 | Mg8Dy1Eu1Zn0.2Zr | 3.88 ± 1.87 |
| L22 | Mg10Dy1.5Nd1Zn0.2Zr0.05Fe | 4.47 ± 2.11 |
| L34 | Mg12Dy1Eu0.8Zn0.2Zr | 5.46 ± 1.22 |
| L29 | Mg6Dy4Eu1Zn0.2Zr | 12.20 ± 1.36 |
| L33 | Mg10Dy0.3Eu1.5Nd1Zn0.2Zr | 1.25 ± 0.67 |
| L26 | Mg5Dy2.5Eu | 23.56 ± 1.56 |
| L31 | Mg25Dy0.4Nd1.4Eu | 48.71 ± 1.87 |

Example 6

Mechanical Characteristics of the Alloys

The alloys and cast parts were produced according to Example 1 and extruded. The heat treatment T4 was carried out at 510° C. over 8 hours and eventually afterwards the heat treatment T6 at 200° C. over a period of time of 72 hours. After T4 heat treatment the samples were immediately quenched in water. All samples were taken from the same position of the blocks.

The tensile tests were performed at room temperature according to DIN EN 10002-1 (corresponds to ISO 6892 and ASTM E8) and compression tests were performed at room temperature according to DIN 50106 (corresponds to ISO 604 and ASTM D695). At least 3 samples were tested for each value. The tensile strength was calculated in terms of the maximum tensile force achieved in the tensile test in regard to the original cross-section of the sample.

TABLE 2

Mechanical characteristics of alloys according to the invention. Alloys were tested as a sample after the extrusion (ST, without heat treatment) and after different heat treatments, T4 (solution annealed), and T6 (a further heat treatment after T4, also known as "ageing"). The information on the components of the alloys are in % by wt. and Mg as the main component complements the quantitative data always up to 100% of the alloy. SD means standard deviation of the average values, which are indicated in the left column (n = 3).

|  | Composition | Yield strength (MPa) | SD | Tensile strength (MPa) | SD | Break at elongstion (%) | SD |
|---|---|---|---|---|---|---|---|
| ST | Mg8Dy1Nd0.2 Zn0.2Zr | 107.33 | 1.8 | 208.5 | 0.85 | 28.12 | 3.41 |
| T4 |  | 87.54 | 0.46 | 176.84 | 2.03 | 18.83 | 1.79 |
| T6 |  | 97.95 | 1.67 | 194.11 | 1.1 | 19.33 | 0.68 |
| ST | Mg10Dy1Nd1Eu1Zn0.2Zr | 169.30 | 0.74 | 283.89 | 0.68 | 16.96 | 1 |
| T4 |  | 151.97 | 1.77 | 259.50 | 2.57 | 18.02 | 0.29 |
| T6 |  | 159.23 | 2.23 | 275.55 | 1.78 | 18.15 | 2.77 |
| ST | Mg12Dy1Nd1Zn0.2Zr | 126.07 | 1.8 | 226.04 | 0.35 | 28.55 | 0.08 |
| T4 |  | 98.38 | 0.43 | 188.45 | 0.5 | 20.47 | 0.91 |
| T6 |  | 114.6 | 1.69 | 205.2 | 1.25 | 17.99 | 0.79 |
| ST | Mg8Dy1Nd1Eu1Zn0.1Zr | 132.24 | 1.1 | 227.21 | 0.59 | 19.75 | 1.11 |
| T4 |  | 114.93 | 1.25 | 210.73 | 1.51 | 20.89 | 1.01 |
| T6 |  | 136.77 | 1.77 | 223.28 | 0.67 | 23.64 | 2.01 |
| ST | Mg6Dy1Nd1Eu1.5Zn0.4Zr | 128.14 | 8.02 | 202.74 | 2.91 | 24.62 | 2.09 |
| T4 |  | 80.97 | 2.27 | 173.47 | 2.02 | 23.78 | 3.52 |
| T6 |  | 84.26 | 2.57 | 178.26 | 1.35 | 26.32 | 2.5 |
| ST | Mg14Dy0.5Nd0.5Eu2Zn0.2Zr | 165.64 | 4.95 | 218.17 | 3.07 | 18.9 | 1.14 |
| T4 |  | 110.78 | 1.87 | 201.28 | 1.19 | 21.62 | 1.07 |
| T6 |  | 153.15 | 3.55 | 264.09 | 0.71 | 17.66 | 1.33 |
| ST | Mg10Dy1.5Nd1Zn0.05Fe | 145.46 | 3.55 | 237.21 | 0.75 | 28.9 | 1.73 |
| T4 |  | 102.78 | 4.38 | 193.36 | 5.84 | 27.57 | 0.88 |
| T6 |  | 108.84 | 1.68 | 200.16 | 2.97 | 25.56 | 1.66 |
| ST | Mg4.5Dy0.5Nd | 68.39 | 7.9 | 208.48 | 2.03 | 28.4 | 0.72 |
| T4 |  | 60.31 | 1.71 | 179.04 | 0.83 | 23.17 | 0.38 |
| T6 |  | 75.13 | 1.32 | 250.34 | 1.42 | 13.34 | 0.74 |
| ST | Mg15Dy0.9Nd1Zr1Zn | 136.93 | 1.6 | 227.07 | 0.42 | 22.9 | 3.03 |
| T4 |  | 95.79 | 1.94 | 200.59 | 2.59 | 21.57 | 0.34 |
| T6 |  | 112.09 | 0.41 | 206.11 | 0.19 | 19.56 | 0.66 |
| ST | Mg20Y0.9Eu | 159.75 | 1.99 | 238.55 | 0.76 | 11.57 | 0.58 |
| T4 |  | 123.19 | 4.83 | 214 | 1.42 | 19.62 | 2.74 |
| T6 |  | 144.08 | 4.37 | 220.2 | 2.58 | 15.58 | 0.94 |
| ST | Mg20Gd5Nd1Zn2Zr | 297.75 | 8.12 | 338.53 | 5.67 | 1.53 | 0.27 |
| T4 |  | 195.82 | 15.65 | 276.89 | 0.91 | 6.58 | 0.95 |
| T6 |  | 327.07 | 17.57 | 378.45 | 14.94 | 0.76 | 0.32 |
| ST | Mg8Dy1Eu1Zn0.2Zr | 112.85 | 1.15 | 198.9 | 0.43 | 24.07 | 1.05 |
| T4 |  | 93.5 | 1.01 | 182.38 | 0.91 | 24.02 | 0.81 |
| T6 |  | 99 | 0.99 | 185.7 | 0.4 | 25.9 | 1.16 |
| ST | Mg10Dy1.5Nd1Zn0.2Zr0.05Fe | 127.8 | 4.62 | 215.84 | 1 | 19.39 | 1.4 |
| T4 |  | 96.72 | 4.02 | 192.99 | 2.87 | 25.92 | 0.98 |
| T6 |  | 112.34 | 3.1 | 201.35 | 2.18 | 24.44 | 1.91 |
| ST | Mg12Dy1Eu0.8Zn0.2Zr | 182.30 | 1.52 | 293.62 | 1.37 | 22.39 | 2.06 |
| T4 |  | 164.48 | 1.44 | 268.66 | 0.45 | 23.70 | 1.63 |
| T6 |  | 172.34 | 2.12 | 271.35 | 1.82 | 23.34 | 1.79 |
| ST | Mg6Dy4Eu1Zn0.2Zr | 115.09 | 1.39 | 208.3 | 1.68 | 2.30 | 0.51 |
| T4 |  | 97.55 | 0.74 | 189.39 | 0.84 | 4.78 | 1.71 |
| T6 |  | 112.58 | 1.59 | 196.71 | 2.31 | 3.41 | 0.69 |
| ST | Mg10Dy0.3Eu1.5Nd1Zn0.2Zr | 168.54 | 6.15 | 277.11 | 2.09 | 16.46 | 2.33 |
| T4 |  | 136.36 | 5.11 | 244.89 | 2.37 | 20.67 | 3.15 |
| T6 |  | 152.22 | 2.42 | 253.91 | 2.33 | 18.56 | 1.87 |
| ST | Mg5Dy2.5Eu | 74.25 | 1.63 | 283.50 | 1.44 | 21.60 | 1.27 |
| T4 |  | 60.19 | 1.69 | 264.46 | 0.91 | 23.16 | 1.43 |
| T6 |  | 65.38 | 1.83 | 266.64 | 1.36 | 22.85 | 1.64 |
| ST | Mg25Dy0.4Nd1.4Eu | 106.34 | 2.98 | 211.15 | 1.65 | 18.90 | 1.55 |
| T4 |  | 88.74 | 1.69 | 178.56 | 2.03 | 20.03 | 2.31 |
| T6 |  | 94.21 | 1.34 | 191.25 | 1.67 | 19.54 | 1.99 |

Example 7

Animal Study 8 stents prepared according to Example 2 and 3 were implanted in the coronary arteries of 4 domestic pigs. The stents had a diameter of 3.0 mm and a length of 14 mm (length of the catheter balloon 15 mm), were not coated (BMS), and were made of an alloy of the following composition:

| | |
|---|---|
| 87.8 Gew.-% | magnesium |
| 10.0 Gew.-% | dysprosium |
| 1.0 Gew.-% | neodymium |
| 1.0 Gew.-% | zinc |
| 0.2 Gew.-% | zirconium |

The "follow up" period has been chosen for all 4 animals at 4 weeks after implantation. One day prior to stent implantation a single dose of Clopidogrel (300 mg) and Aspirin (250 mg) were administered orally. Under general anaesthesia, access to the femoral artery was obtained by surgical exposure and a bolus of heparin sodium (10 000 IU) was administered. A 6F coronary guiding catheter was inserted through the femoral artery into the Aorta descendens. Coronary angiography was performed using hand injection of nonionic contrast agent to obtain the anatomic conditions for performance of the procedure.

The stents were implanted in the ramus interventricularis anterior (RIVA or LAD) and ramus circumflexus (RCX or LCx). Inflation pressure of the balloon for stent implantation was chosen to achieve a stent balloon to artery ratio of 1.2 to 1. The pigs were then allowed to recover. During the entire 4 weeks of "follow up", the animals receive orally a daily dose of 100 mg aspirin and 75 mg clopidogrel per 30 g body weight.

After 4 weeks "follow up", control angiography and optical coherence tomography (OCT) were performed. In the OCT procedure a 0.014 inch guidewire was inserted into the LAD and the LCx and pushed through the implanted stent into the distal part of the vessel. An OCT intravascular catheter was subsequently advanced distal to the stent, over the guide wire. The injection pump was turned on to inject contrast agents at a speed of 3.0 ml/s to transiently displace the blood. The entire length of the lesion was imaged using an automatic pullback device at 10 mm/s. After imaging, the OCT catheter was withdrawn, and the images were saved. The animals were then euthanized, and the coronary arteries were explanted.

The explanted arteries were fixed by perfusion with a pressure of 100 mmHg for 1 h using 7% formalin. The stents were processed for light microscopy. For light microscopy, the arteries were cut into 3 sections: proximal, mid and distal stent segments.

The stented sections were embedded in methyl-metacrylate (Technovit 9100). The segments of the stented arteries were cut into 4-6 µm slices using a rotary microtome, and stained with hematoxylin and eosin.

As part of the analysis details of the study were listed such as the stent position, the dilation pressure and the inflation time, as well as any complications during the implantation.
Quantitative Coronary Angiography (QCA)

A QCA was performed to analyze the in-stent restenosis. The following parameters were thereby determined: vessel diameter pre and post stent implantation, minimal lumen diameter (MLD) after stent implantation and at follow up and the diameter of a reference segment (RD) at follow up. Here, the minimal lumen diameter is the smallest absolute internal vessel diameter in the region of the dilated segment, averaged from the two orthogonal projection planes. LLL (late lumen loss) is a measure of the narrowing of the lumen by neointimal hyperplasia. The lumen diameter is measured directly after the intervention and 4 weeks post interventional, the difference between the two is given as LLL. The length of the stenosed or dilated segment has been checked and the stenosis in percent was calculated.
Optical Coherence Tomography (OCT)

The images of the optical coherence tomography were analyzed in accordance with the relevant guideline (JACC, 2012). The following parameters were obtained: stent malapposition, stent strut coverage, tissue protrusion, the arterial dissection, thrombosis. The quantitative analysis of the OCT images includes the minimal and maximal stent diameter and the lumen area. The following parameters were calculated: maximal area stenosis and stent symmetry. For the quantitative analysis the "worst" cross-section per test group was determined.

% AS=Intimal area/Stent area=(Stent area−lumen area)/Stent area    Calculation of area stenosis (% AS):

Stent symmetry=(Maximal Stent diameter−Minimal stent diameter)/Maximal stent diameter    Calculation of stent symmetry:

Fibrin deposition, degree of inflammation (intima and adventitia), haemorrhages and necrosis were analyzed in accordance with the published guidelines.
Histomorphometry Histomorphometry has been carried out using computer-assisted planimetry. The lumen, the area of the internal elastic lamina and external elastic lamina and the maximal neointimal thickness were measured. The extension of the neointima and the media as well as the stenosis in percent was calculated.
Results The dilation pressure used was between 12 and 18 atm. The balloon inflation took 30 sec. In general, the handling of the stent and balloon were excellent; very good pushability and very short deflation time was recorded.

TABLE 3

Results of quantitative coronary angiography (QCA), the average values and standard deviations (SD) are listed; MLD = minimal lumen diameter, RD = diameter of a reference segment, % DS = percent diameter stenosis, FUP = follow-up, LLL = late lumen loss

| | Pre-MLD (mm) | Post-MLD (mm) | FUP-MLD (mm) | FUP-RD (mm) | FUP-% DS (%) | LLL (mm) |
|---|---|---|---|---|---|---|
| bare metal stents (BMS) | 2.68 | 2.93 | 2.08 | 2.92 | 28.75 | 0.85 |
| SD | 0.11 | 0.07 | 0.53 | 0.20 | 16.79 | 0.47 |

TABLE 4

Qualitative analysis of the optical coherence tomography (OCT) per implanted stent

| animal No. | artery | group | stent-malapposition | tissue protrusion | in-stent thrombosis | in-stent dissection | edge dissection | endothelialization |
|---|---|---|---|---|---|---|---|---|
| MEKO-1 | LAD | BMS | 0 | 0 | 0 | 0 | 0 | complete |
| MEKO-1 | LCx | BMS | 0 | 0 | 0 | 0 | 0 | incomplete |
| MEKO-2 | LAD | BMS | 0 | 0 | 0 | 0 | 0 | complete |
| MEKO-2 | LCx | BMS | 0 | 0 | 0 | 0 | 0 | complete |
| MEKO-3 | LAD | BMS | 0 | 0 | 0 | 0 | 0 | complete |
| MEKO-3 | LCx | BMS | 0 | 0 | 0 | 0 | 0 | complete |
| MEKO-4 | LAD | BMS | 0 | 0 | 0 | 0 | 0 | complete |
| MEKO-4 | LCx | BMS | 0 | 0 | 0 | 0 | 0 | complete |

TABLE 5

Qualitative analysis of the optical coherence tomography (OCT) in regard to the number of implanted stents (n = 8, all values in percent)

| | stent-malapposition | tissue protrusion | in-stent thrombosis | in-stent dissection | edge dissection | completed endothelialization |
|---|---|---|---|---|---|---|
| BMS n = 8 | 0 | 0 | 0 | 0 | 0 | 87.5 |

From Tables 3, 4 and 5 can be gathered that firstly none of the tested complications occurred when using a stent according to the invention and, secondly, that an endothelialization was almost always completed after 4 weeks, which meant that the increased risk of in-stent thrombosis due to not completed endothelialization or inflammation reactions was no longer present. Comparable results were also obtained with stents made of a magnesium alloy containing europium instead of neodymium.

TABLE 6

Further results of the qualitative analysis of the optical coherence tomography (OCT), listed are average values and standard deviations (SD).

| Type | minimal stent diameter (mm) | maximal stent diameter (mm) | stent area (mm$^2$) | lumen area (mm$^2$) | % AS (%) | stent symmetry |
|---|---|---|---|---|---|---|
| BMS n = 8 | 2.54 | 2.72 | 7.58 | 5.08 | 34.0 | 0.07 |
| SD | 0.34 | 0.35 | 1.80 | 1.69 | 13.2 | 0.02 |

The invention claimed is:

1. Absorbable stent consisting of a magnesium alloy which consists of the following components based on the total weight of the alloy:

| | |
|---|---|
| 5.0% by wt.-25.5% by wt. | dysprosium |
| 0.01% by wt.-5.0% by wt. | neodymium and/or europium |
| 0.1% by wt.-3.0% by wt. | zinc |
| 0.1% by wt.-2.0% by wt. | zirconium |
| 1 ppm-0.4% by wt. | impurities |
| balance to 100.0% by wt. | magnesium, | wherein the alloy contains in total not more than 0.1% per wt. of the elements terbium, holmium, erbium, thulium, ytterbium and lutetium, and wherein the alloy contains no yttrium and no gadolinium.

2. Absorbable stent of a magnesium alloy according to claim 1 comprising:

| | |
|---|---|
| 0.1% by wt.-2.0% by wt. | zinc. |

3. Absorbable stent of a magnesium alloy according to claim 1 comprising:

| | |
|---|---|
| 0.1% by wt.-0.3% by wt. | zirconium. |

4. Absorbable stent of a magnesium alloy according to claim 1 consisting of:

| | |
|---|---|
| 80.7% by wt.-94.7% by wt. | magnesium |
| 5.0% by wt.-15.0% by wt. | dysprosium |
| 0.1% by wt.-2.0% by wt. | neodymium |
| 0.1% by wt.-2.0% by wt. | zinc |
| 0.1% by wt.-0.3% by wt. | impurities | wherein the alloy contains no yttrium and no gadolinium.

5. Absorbable stent of a magnesium alloy according to claim 1 consisting of:

| | |
|---|---|
| 80.4% by wt.-94.6% by wt. | magnesium |
| 5.0% by wt.-15.0% by wt. | dysprosium |
| 0.1% by wt.-2.0% by wt. | neodymium and/or europium |

-continued

| | |
|---|---|
| 0.1% by wt.-2.0% by wt. | zinc |
| 0.1% by wt.-0.3% by wt. | zirconium |
| 0.1% by wt.-0.3% by wt. | impurities | wherein the alloy contains no yttrium and no gadolinium.

6. Absorbable stent according to claim 1, wherein the absorbable stent is a stent for blood vessels, urinary tracts, respiratory tracts, biliary tracts or the digestive tract.

* * * * *